(12) United States Patent
Turbett

(10) Patent No.: US 9,724,438 B2
(45) Date of Patent: Aug. 8, 2017

(54) STERILIZING METHOD AND APPARATUS

(71) Applicant: Turbett Surgical LLC, Rochester, NY (US)

(72) Inventor: Robert E. Turbett, Penfield, NY (US)

(73) Assignee: TURBETT SURGICAL LLC, Rochester, NY (US)

( * ) Notice: Subject to any disclaimer, the term of this patent is extended or adjusted under 35 U.S.C. 154(b) by 0 days.

(21) Appl. No.: 14/675,048

(22) Filed: Mar. 31, 2015

(65) Prior Publication Data
US 2015/0209456 A1    Jul. 30, 2015

Related U.S. Application Data

(63) Continuation-in-part of application No. 14/584,751, filed on Dec. 29, 2014, which is a continuation-in-part of application No. 14/167,691, filed on Jan. 29, 2014.

(51) Int. Cl.
| | |
|---|---|
| *A61B 17/06* | (2006.01) |
| *A61L 2/00* | (2006.01) |
| *A61L 9/00* | (2006.01) |
| *A61L 2/07* | (2006.01) |

(52) U.S. Cl.
CPC ............. *A61L 2/07* (2013.01); *A61L 2202/24* (2013.01)

(58) Field of Classification Search
CPC ............. A61L 2/00; A61L 2/0017; A61L 2/07
USPC ......... 422/1, 26, 28, 297, 300, 307; 206/439
See application file for complete search history.

(56) References Cited

U.S. PATENT DOCUMENTS

| | | |
|---|---|---|
| 2,981,196 A | 4/1961 | Zimmermann et al. |
| 3,351,422 A | 11/1967 | Jones et al. |
| 4,643,303 A | 2/1987 | Arp et al. |
| 4,670,227 A | 6/1987 | Smith |

(Continued)

FOREIGN PATENT DOCUMENTS

| | | |
|---|---|---|
| CA | 2759434 A1 | 11/2010 |
| DE | 202004002095 U1 | 4/2004 |

(Continued)

OTHER PUBLICATIONS

International Search Report and Written Opinion of the International Searching Authority in corresponding International Application No. PCT/US2015/010464; mailed Apr. 3, 2015 (9 pages).

(Continued)

*Primary Examiner* — Monzer R Chorbaji
(74) *Attorney, Agent, or Firm* — Brian B. Shaw, Esq.; Jodi A. Reynolds, Esq.; Harter Secrest & Emery LLP

(57) ABSTRACT

Methods and apparatus for sterilization are presented. An apparatus includes a sterilizing cabinet assembly including a cabinet having an access port and a bottom, the bottom configurable to induce a condensate to flow on the bottom to a vent port. The apparatus further includes a door connected to the cabinet, the door moveable between an open position permitting passage through the access port to an interior of the cabinet and a closed position precluding passage through the access port. The apparatus also includes at least one of the cabinet and the door having the vent port, and a filter overlying the vent port and forming a sealed interface with an adjacent portion of the one of the cabinet and the door.

20 Claims, 33 Drawing Sheets

(56) References Cited

U.S. PATENT DOCUMENTS

| | | |
|---|---|---|
| 4,728,504 A | 3/1988 | Nichols |
| 4,997,240 A | 3/1991 | Schmalzl |
| 5,205,627 A | 4/1993 | Davidson |
| 5,346,075 A * | 9/1994 | Nichols ................. A61B 50/31 206/363 |
| 5,417,729 A | 5/1995 | Greenleaf, Sr. |
| 5,843,388 A | 12/1998 | Arroyo et al. |
| 5,893,618 A | 4/1999 | LePage, Jr. et al. |
| 5,968,459 A | 10/1999 | Nalepa et al. |
| 6,196,303 B1 | 3/2001 | Hepper |
| 6,572,819 B1 | 6/2003 | Wu et al. |
| 6,620,390 B1 | 9/2003 | Wagner |
| 6,789,815 B2 | 9/2004 | Moss |
| 8,454,901 B1 | 6/2013 | Snyder, III |
| 9,439,992 B2 | 9/2016 | Webb et al. |
| 2004/0001783 A1 | 1/2004 | Bowen |
| 2004/0011689 A1 | 1/2004 | Bauer |
| 2004/0178137 A1 | 9/2004 | Itoh et al. |
| 2004/0256270 A1 | 12/2004 | Gleichauf et al. |
| 2005/0238530 A1 | 10/2005 | Frieze et al. |
| 2007/0039294 A1 | 2/2007 | Airey |
| 2008/0104990 A1 | 5/2008 | Lee et al. |
| 2009/0223972 A1* | 9/2009 | Allen ........................ A61L 2/26 220/529 |
| 2012/0174922 A1 | 7/2012 | Virr et al. |
| 2013/0322004 A1 | 12/2013 | Park |
| 2015/0107627 A1 | 4/2015 | Snyder |
| 2015/0209456 A1 | 7/2015 | Turbett |
| 2015/0314026 A1 | 11/2015 | Mauzerall et al. |
| 2016/0008503 A1 | 1/2016 | Webb et al. |
| 2016/0346415 A1 | 12/2016 | Webb et al. |

FOREIGN PATENT DOCUMENTS

| | | |
|---|---|---|
| FR | 2986147 A1 | 8/2013 |
| GB | 272284 | 6/1927 |
| JP | 4189453 B2 | 12/2008 |
| WO | 2007/045943 A1 | 4/2007 |
| WO | 2010/128408 A1 | 11/2010 |

OTHER PUBLICATIONS

USPTO Office Action dated Jan. 21, 2016 in corresponding U.S. Appl. No. 14/167,691.

Aesculap Surgical Technologies SterilContainerSystem, archived on Jan. 24, 2013 accessed at http://web.archive.org/web/20130124053037/http://www.aesculapusa.com/assets/base/doc/DOC132RevD-SterilContainerSystem.pdf.

USPTO Office Action dated Jul. 7, 2016 in U.S. Appl. No. 14/644,094 11 pages.

USPTO Office Action dated Aug. 12, 2016 in corresponding U.S. Appl. No. 14/167,691 28 pages.

International Search Report and Written Opinion of the International Searching Authority in corresponding PCT Application No. PCT/US16/25262 dated Jul. 5, 2016 (10 pages).

* cited by examiner

STERILIZING METHOD AND APPARATUS

STATEMENT REGARDING FEDERALLY SPONSORED RESEARCH OR DEVELOPMENT

None.

REFERENCE TO A "SEQUENCE LISTING"

None.

FIELD OF THE INVENTION

Exemplary embodiments of the present invention relate to a method and apparatus for sterilization and more particularly to a method and apparatus for sterilization of instruments.

BACKGROUND OF THE INVENTION

Sterilization is a term referring to any process that eliminates (removes) or kills microbial life, including transmissible agents (such as fungi, bacteria, viruses, or spore forms) present on a surface, or contained in a fluid, or in medication, or in a compound such as biological culture media. Sterilization can be achieved by applying heat, chemicals, irradiation, high pressure, and filtration or combinations thereof.

In general, surgical instruments and medications that enter an already aseptic part of the body (such as the bloodstream, or penetrating the skin) must be sterilized to a high sterility assurance level. Examples of such instruments include scalpels, hypodermic needles and implantable medical devices (IMD), such as artificial pacemakers.

A widely used method for heat sterilization is the autoclave, sometimes referred to as a converter. Autoclaves commonly use steam heated to 121-134° C. To achieve a degree of sterility, a holding time of at least 15 minutes at 121° C. at 100 kPA, or 3 minutes at 134° C. at 100 kPa is required. Additional sterilizing time is usually required for liquids and instruments packed in layers of cloth, as they may take longer to reach the required temperature.

One method of sterilization involves passing steam through a cabinet. For effective sterilization, steam needs to penetrate the cabinet load uniformly. Accordingly, the cabinet must not be overcrowded, and the lids of bottles and containers must be left ajar. During the initial heating of the chamber, residual air must be removed. Indicators should be placed in the most difficult places for the steam to reach to ensure that steam actually penetrates there.

A filter is typically placed over the vent to keep particles or extraneous materials from entering the cabinet before, during or after the sterilizing process. Once the sterilizing process is completed the filter needs to be removed and inspected by medical professionals to verify the integrity of the sterilizing process was maintained. If it is discovered during inspection that the filter did not remain intact, the sterilizing process has to be repeated with a new filter.

SUMMARY OF THE INVENTION

In view of the foregoing, it is an object of the present invention to provide a method and apparatus for sterilization.

A first exemplary embodiment of the present invention provides a sterilizing cabinet assembly. The sterilizing cabinet assembly includes a cabinet having an access port and a door connected to the cabinet, the door moveable between an open position permitting passage through the access port to an interior of the cabinet and a closed position precluding passage through the access port. This embodiment further includes at least one of the cabinet and the door having a vent port and a primary filter overlying the vent port and forming a sealed interface with an adjacent portion of the one of the cabinet and the door. This embodiment further includes a secondary filter overlying at least a portion of the primary filter. In this embodiment, the secondary filter forms an independent sealed interface with the sterilizing cabinet or the primary filter.

A second exemplary embodiment of the present invention provides a method for placing filters. The method includes disposing a primary filter to occlude a vent port of a sterilizing cabinet forming a first sealed interface with the sterilizing cabinet. The method further includes forming a second sealed interface between a confirmatory filter and at least a portion of one of the sterilizing cabinet and the primary filter, a portion of the confirmatory filter overlying a portion of the primary filter. In this embodiment, the second sealed interface is independent of the first sealed interface.

A third exemplary embodiment of the present invention provides a sterilizing assembly. The sterilizing assembly includes a sterilizing cabinet and a first tray and a second tray sized to be retained within the cabinet. The sterilizing assembly further includes at least one removable spacer intermediate the first tray and the second tray, the spacer being sterilizable and vertically separating the first tray and the second tray by a given height, the spacer inhibiting lateral displacement of the first tray relative to the second tray, wherein the given height is sufficient to permit a passage of a sufficient amount of a sterilizing agent between the first tray and the second tray for a predetermined time.

A fourth exemplary embodiment of the present invention provides a method of loading a sterilizing cabinet. The method includes loading a sterilizable first pan and a sterilizable second pan within the sterilizing cabinet. The method further includes placing a removable and sterilizable spacer between the first pan and the second pan, the spacer (i) providing at least one of a predetermined vertical spacing between the first pan and the second pan and (ii) inhibiting horizontal displacement of the first pan relative to the second pan.

A fifth exemplary embodiment of the present invention provides a method of sterilizing. The method includes loading a tray retaining a surgical instrument in a sterilization cabinet and sealing a primary filter relative to a vent port in the sterilization cabinet. The method further includes sealing a secondary filter relative to the vent port and independent of the sealed primary filter and passing a sterilizing agent through the secondary filter and the primary filter.

A sixth exemplary embodiment of the present invention provides a sterilizable pan assembly. The sterilizable pan assembly includes a first sterilizable pan having an open top, a closed bottom and a pair of projecting spacer legs and a second sterilizable pan having an open top and closed bottom. The sterilizable pan assembly further includes the spacer legs configured to releasably engage a portion of the second pan and maintain a predetermined vertical spacing between the bottom of the first pan and the top of the second pan.

A seventh exemplary embodiment of the present invention provides a filtering assembly. The filtering assembly including a primary filter holding portion for holding a primary filter for overlying a vent port and forming a sealed interface with a sterilizing cabinet. The filter assembly further includes a secondary filter holding portion for holding a secondary filter, moveably attached to the primary holding portion for overlying the primary filter holding portion and forming a sealed interface with the primary filter holding portion.

An eighth exemplary embodiment of the present invention provides a method for verifying sterilization. The method includes performing a sterilization cycle in a sterilization device. The method further includes removing a secondary filter that is overlying a primary filter with a second sealed interface with the primary filter from the sterilizing device such that the primary filter maintains a sealed interface with a vent port of the sterilizing device and examining the secondary filter to verify the integrity of the sterilization cycle in the sterilizing device.

A ninth exemplary embodiment of the present invention provides a sterilizing cabinet assembly. The sterilizing cabinet assembly includes a cabinet having an access port and a door connected to the cabinet, the door moveable between an open position permitting passage through the access port to an interior of the cabinet and a closed position precluding passage through the access port. The sterilizing cabinet assembly further includes at least one of the cabinet and the door having a vent port and a filter overlying the vent port and forming a sealed interface with an adjacent portion of the one of the cabinet and the door.

A tenth exemplary embodiment of the present invention provides a method of placing filters. The method includes disposing a primary door to occlude a vent port of a sterilizing cabinet, the primary door comprising an edge portion and an internal portion, the internal portion comprising a plurality of openings. The method further includes disposing a filter over the primary door to occlude the vent port of the sterilizing cabinet and disposing a secondary door over the filter and the primary door to occlude the vent port of the sterilizing cabinet forming a sealed interface with the filter, the primary door and the sterilizing cabinet.

An eleventh exemplary embodiment of the present invention provides a method of verifying sterilization. The method includes performing a sterilization cycle in a sterilizing device. The method further includes removing a secondary door that is overlying a filter with a second sealed interface with the filter from the sterilizing device. The method still further includes examining the filter to verify the integrity of the sterilization cycle in the sterilizing device.

A twelfth exemplary embodiment provides a sterilizing cabinet assembly including a cabinet having an access port and a bottom, the bottom configurable to induce condensate to flow on the bottom to pass through a vent port. The sterilizing cabinet assembly further includes a door connected to the cabinet, the door moveable between an open position permitting passage through the access port to an interior of the cabinet and a closed position precluding passage through the access port, and at least one of the cabinet and the door having the vent port. The sterilizing cabinet assembly can also include a filter overlying the vent port to form a sealed interface with an adjacent portion of the one of the cabinet and the door.

A thirteenth exemplary embodiment provides a method of sterilizing. The method includes disposing a primary door to occlude a vent port of a sterilizing cabinet, the primary door comprising an edge portion and an internal portion, the internal portion comprising a plurality of openings, the sterilizing cabinet having a bottom configurable to induce a flow of condensate on the bottom to the vent port. The method also includes disposing a filter over the primary door to occlude the vent port of the sterilizing cabinet. The method further includes performing a sterilizing cycle on the sterilizing cabinet, and draining resulting condensate through the filter.

A fourteenth exemplary embodiment provides a method for sterilizing. The method includes generating a condensate in a sterilizing cabinet, the sterilizing cabinet being within a closed autoclave, and draining the condensate through a vent port of the sterilizing cabinet prior to opening the autoclave. It is contemplated the vent port can include a filter.

A further embodiment provides a sterilizing cabinet assembly, including a cabinet having an access port and a bottom; a door connected to the cabinet, the door moveable between an open position permitting passage through the access port to an interior of the cabinet and a closed position precluding passage through the access port; at least one of the cabinet and the door having a vent port, wherein the bottom induces condensate on the bottom to flow to the vent port; and a filter overlying the vent port and forming a sealed interface with an adjacent portion of the one of the cabinet and the door.

A method of sterilizing, is provided including occluding a vent port of a sterilizing cabinet with a filter, the sterilizing cabinet having an internal inclined surface to induce a condensate flow to the vent port; performing a sterilization cycle on the sterilizing cabinet; and draining at least a portion of a condensate formed in the sterilization cycle along the inclined surface to pass from the sterilizing cabinet through the filter.

Another method includes locating a sterilizing cabinet in an autoclave; applying a sterilization cycle to the sterilizing cabinet in the autoclave; and draining along an inclined surface in the sterilizing cabinet at least a portion of a condensate from the sterilizing cabinet during the sterilization cycle.

The following will describe embodiments of the present invention, but it should be appreciated that the present invention is not limited to the described embodiments and various modifications of the invention are possible without departing from the basic principle. The scope of the present invention is therefore to be determined solely by the appended claims.

BRIEF DESCRIPTION OF THE SEVERAL VIEWS OF THE DRAWING(S)

DETAILED DESCRIPTION OF THE INVENTION

In the medical field, it is of the utmost importance that medical instruments are sterilized prior to any medical procedure. This drastically helps prevent the spread of infectious materials. In the marketplace, there are a wide variety of devices that provide for sterilization of medical instruments through the use of a sterilizing agent, such as steam. Instrument trays can be wrapped in a cloth or paper that acts as a filter, allowing the tray to be sterilized, then delivered to the operating room. Alternatively, a rigid container can contain the instrument tray. Typically, the device (e.g., a rigid container) contains a vent for venting the steam used to sterilize the contents of the device. A disposable filter usually covers these vents. The filters have two major purposes. First, they prevent extraneous materials from entering the sterilizing device during and after the sterilization cycle. Second, they allow sterilizing steam to enter and exit the sterilizing device.

However, in order to check that the integrity of the sterilization cycle has been maintained a person (usually a medical technician) must verify that there are no holes or other types of rips in the filter. This is done by removing the filter from the sterilizing device and visually inspecting the filter. This creates an inherent time period wherein the sterilized instruments can be contaminated by extraneous materials that enter the sterilizing device through the now open and uncovered vents. An object of exemplary embodiments of this disclosure provide a solution to this problem.

Figure 1A:
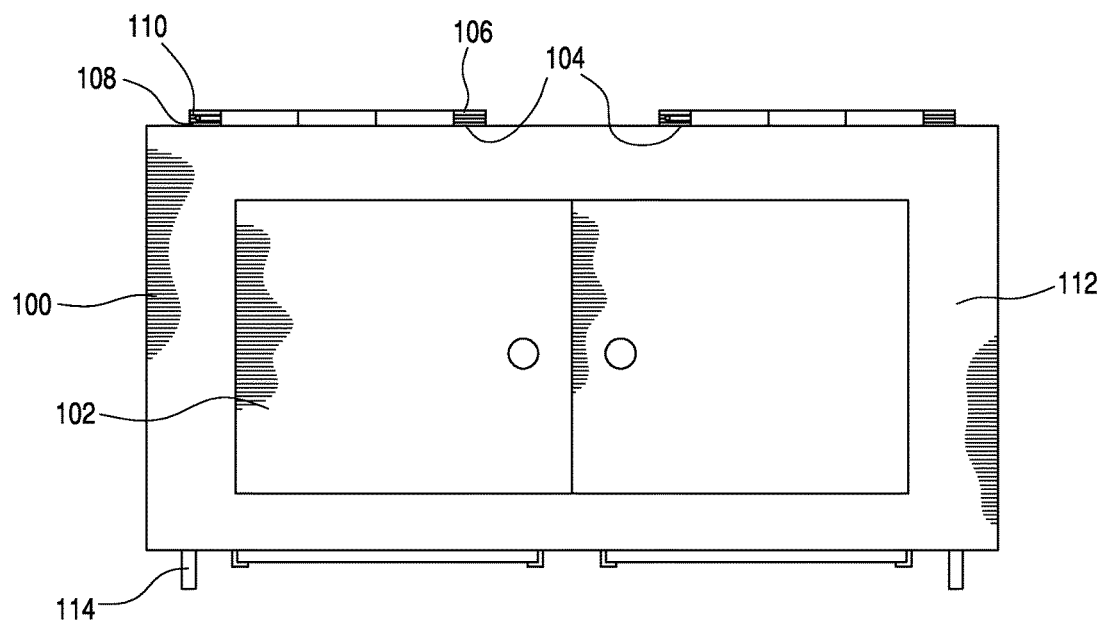
FIG. 1a is a front view of a configuration of a sterilizing cabinet suitable for use in practicing exemplary embodiments of this invention.

Referring to FIG. 1a, is a front view of sterilizing cabinet 100. It should be noted that embodiments of the present invention are not limited to the particular configuration of sterilizing cabinet 100.

The term sterilizing cabinet 100 encompasses any device capable of sterilizing. The term also includes sterilizing cabinets for sterilizing medical instruments, surgical devices and the like.

Sterilizing cabinet 100 includes door or doors 102, vents 104, filter holder 106, primary filter 108, secondary filter 110, sterilizing cabinet frame 112 and legs 114. Door or doors 102 are able to open and close for access to the interior of sterilizing cabinet 100. Door or doors 102 are physically connected to sterilizing cabinet frame 112. Door or doors 102 can be attached through the use of a hinge or hinges which allows the doors to swing open. Alternatively, door or doors 102 can be removable from sterilizing cabinet 100 through the use of clamps (not shown in FIG. 1). It should be appreciated that exemplary embodiments of door or doors 102 include any mechanism that allows for door or doors 102 to move from an open position to a closed position to provide access to the interior of sterilizing cabinet 100.

Sterilizing cabinet 100 in this embodiment provides for four vents 104. However, it should be appreciated that exemplary embodiments of sterilizing cabinet 100 are not limited to four vents. Exemplary embodiments of sterilizing cabinet 100 can include one or more vents. Two vents 104 on the top of sterilizing cabinet 100 and two vents 104 on the bottom of sterilizing cabinet 100. Vents 104 provide numerous small openings for the passage of sterilizing steam. The small openings in vents 104 can be holes or slits. Alternatively, vents 104 can be fenestrated.

Primary filter 108 in conjunction with filter holder 106 covers vent 104. Primary filter 108 with filter holder 106 forms a seal with the adjacent portions of sterilizing cabinet 100 such that during the operation of a sterilizing cycle, any sterilizing steam that passes through the vent 104 must then pass through primary filter 108. Primary filter 108 can be made of a very thin paper. Exemplary embodiments provide that primary filter 108 can be made of any porous material that (1) allows for the passage of sterilizing steam from sterilizing cabinet 100 and (2) prevents extraneous materials from passing through primary filter 108 and entering vent 104. Primary filter 108 is removable from sterilizing cabinet 100 and is typically replaced with a new filter following each sterilizing cycle.

Secondary filter 110 resides on top of primary filter 108 in filter holder 106. Secondary filter 110 covers primary filter 108 and forms a seal with primary filter 108 through filter holder 106 such that any sterilizing steam that passes through the vent 104 must then pass through primary filter 108 and secondary filter 110. Secondary filter 110 can be made of a very thin paper. Secondary filter 110 can be made of any porous material that (1) allows for the passage of sterilizing steam from sterilizing cabinet 100 and primary filter 108 and (2) prevents extraneous materials from passing through secondary filter 108.

Exemplary embodiments of this disclosure provide for secondary filter 110 to form a sealed periphery with primary filter 108. In another exemplary embodiment the sealed interface between the primary filter 108 and the adjacent portion of either the sterilizing cabinet 100 is independent of an interface between secondary filter 110 and primary filter 108. One exemplary arrangement provides for primary filter 108 and secondary filter 110 to be coextensive. In another exemplary embodiment primary filter 108 and secondary filter 110 have different filter properties. For instance, primary filter 108 and secondary filter 110 may filter different elements of the sterilizing agent which exits sterilizing cabinet 100 during a sterilization cycle. In an alternative exemplary embodiment primary filter 108 and secondary filter 110 have similar filter properties. Another exemplary embodiment provides that primary filter 108 and secondary filter 110 are different colors.

In yet another exemplary embodiment, primary filter 108 may be the only filter that covers vent 104. Here, primary filter 108 is removeably held or maintained in place over vent 104 by filter holder 106. In this embodiment, there is no secondary filter. Primary filter 108 forms a seal with the adjacent portions of sterilizing cabinet 100 such that during the operation of a sterilizing cycle, any sterilizing steam that passes through the vent 104 must then pass through primary filter 108. Again, in this embodiment, primary filter 108 can be made of any porous material that (1) allows for the passage of sterilizing steam from sterilizing cabinet 100 and (2) prevents extraneous materials from passing through primary filter 108 and entering vent 104. Primary filter 108 is removable from sterilizing cabinet 100 and is typically replaced with a new filter following each sterilizing cycle.

Legs 114 reside on the bottom of sterilizing cabinet 100 and provide spacing between the surface which sterilizing cabinet 100 rests and the bottom primary filter 108, secondary filter 110 and filter holder 106.

Figure 1B:
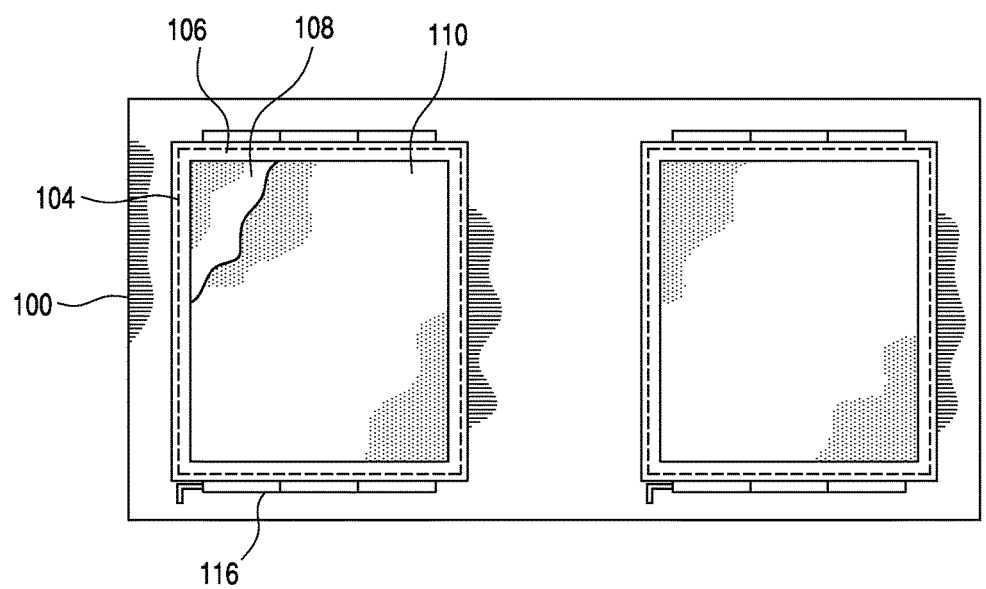
FIG. 1b is a top view of a configuration of a sterilizing cabinet suitable for use in practicing exemplary embodiments of this invention.

FIG. 1b provides a top view of sterilizing cabinet 100 showing vent 104 covered by filter holder 106, primary filter 108, secondary filter 110, sterilizing cabinet frame 112 and hinge 116 of filter holder 106. Hinge 116 with filter holder 106 allows a portion of filter holder 106 to swing open about hinge 116 such that primary filter 108 and secondary filter 110 can be removed independent of one another. In other words, filter holder 106 allows for secondary filter 110 to be released and removed from filter holder 106 while simultaneously maintaining primary filter's 108 seal with sterilizing cabinet 100 over vent 104.

Figure 1C:
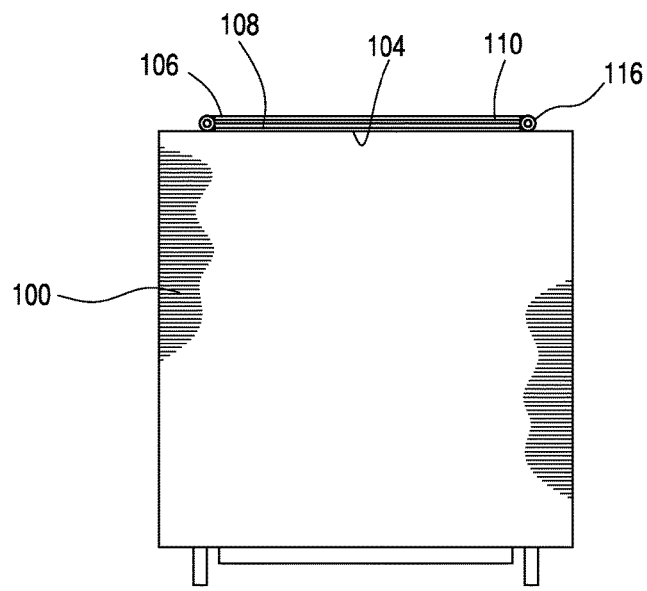
FIG. 1c is a side view of a configuration of a sterilizing cabinet suitable for use in practicing exemplary embodiments of this invention.

FIG. 1c shows a side view of sterilizing cabinet 100 including sterilizing cabinet frame 112, vent 104, primary filter 108, secondary filter 110, filter holder 106 and hinge 116.

In exemplary embodiments sterilizing cabinet 100 may include a steam exposure indicator on either the primary filter 108 or the secondary filter 110 which designates when steam from sterilizing cabinet 100 has passed through one of the filters. An example of one such steam exposure indicator is a tape that changes colors when exposed to steam.

Figure 2A:
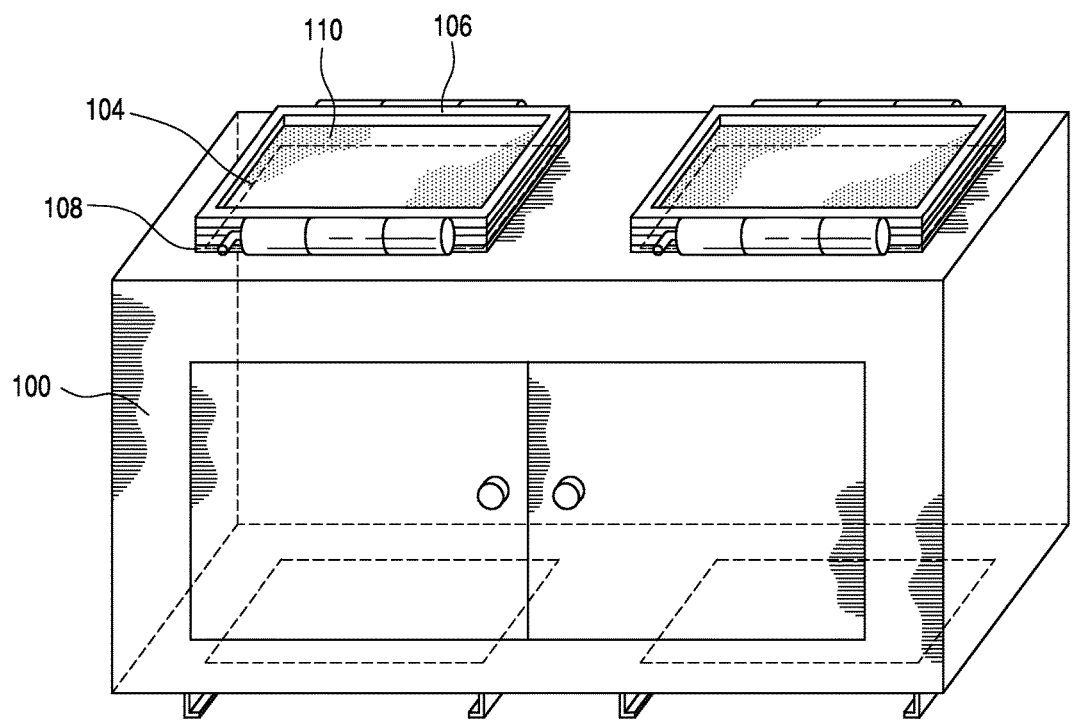
FIG. 2a is a perspective view of an alternative configuration of a sterilizing cabinet suitable for use in practicing exemplary embodiments of this invention.

FIG. 2a provides a perspective view of sterilizing cabinet 100 with two vents 104 on the top and two vents 104 on the bottom of sterilizing cabinet 100. FIG. 2a also includes primary filters 108 occluding vents 104 and secondary filters 110 overlaying primary filters 108 with primary filters 108 and secondary filters 110 each in filter holders 106.

Figure 2B:
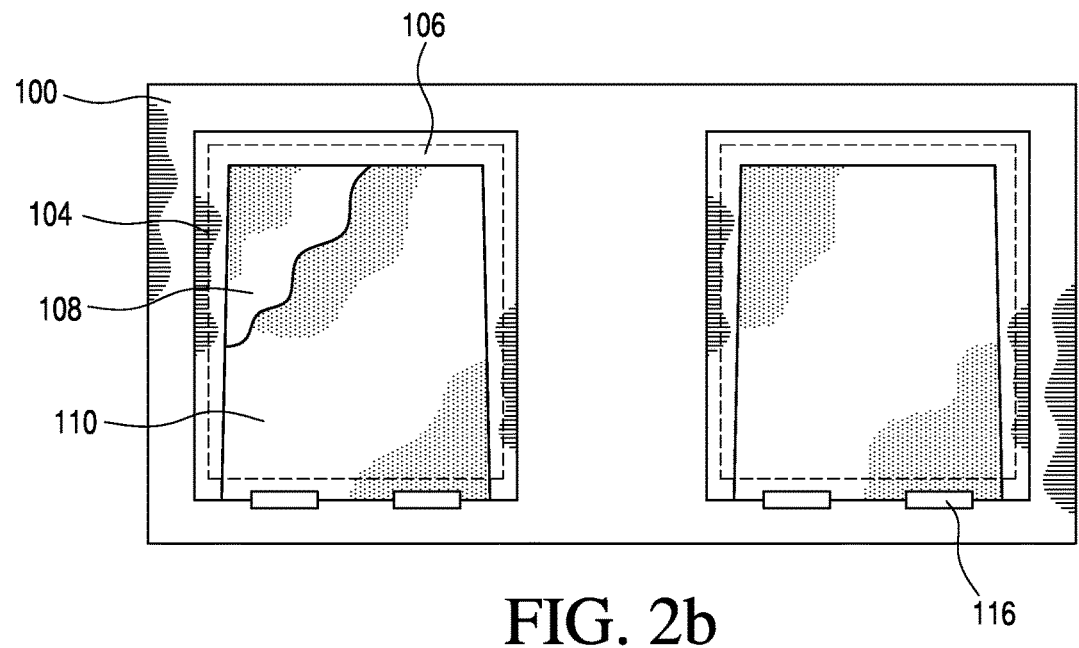
FIG. 2b is a top view of an alternative configuration of a sterilizing cabinet suitable for use in practicing exemplary embodiments of this invention.

FIG. 2b provides a top view of sterilizing cabinet 100 with an alternative exemplary embodiment of filter holder 106. Shown in FIG. 2b are two vents 104 occluded by primary filters 108 which are also covered by secondary filters 110. In this exemplary embodiment filter holders 106 do not have a swinging hinge which allows for the individual attachment and release of primary filters 108 and secondary filters 110. In this exemplary embodiment filter holders 106 allow for independently removing primary filter 108 and secondary filter 110 through the use of a sliding mechanism. Secondary filter 110 can be removed by sliding it out of filter holder 106 while maintaining primary filter's 108 seal with sterilizing cabinet 100 around vent 104.

In another alternative exemplary embodiment, filter holder 106 again does not include a swinging hinge, but allows for the placement and removal of only primary filter 108 by a sliding mechanism. In this embodiment, there is no secondary filter 110. Only primary filter 108 in conjunction with filter holder 106 forms a sealed interface with sterilizing cabinet 100 occluding vents 104. Primary filter 108 can then be placed or removed by sliding into and out of filter holder 106.

In practice, an exemplary embodiment of a process of placing primary filter 108 and secondary filter 110 includes disposing primary filter 108 to occlude a vent 104 of sterilizing cabinet 100 and forming a first sealed interface with the sterilizing cabinet 100. The process continues by forming a second sealed interface between secondary filter 110 (or confirmatory filter) and at least a portion of one of sterilizing cabinet 100 and primary filter 108, a portion of the secondary filter 110 overlying a portion of the primary filter 108. The process can continue by passing a sterilizing agent (typically steam) through primary filter 108 and secondary filter 110 and vent 104.

Also in practice, an exemplary embodiment of a process of placing only a primary filter 108 includes disposing primary filter 108 with filter holder 106 to occlude vent 104 of sterilizing cabinet 100 creating a sealed interface with the sterilizing cabinet 100. The process can continue by passing a sterilizing agent (typically steam) through primary filter 108 and vent 104. The process can then conclude with verifying the integrity of primary filter 108 by either inspecting primary filter 108 while it covers vent 104 in filter holder 106 or after it is removed from filter holder 106. The process may be repeated if it is determined that the integrity of primary filter 108 was compromised during the sterilizing process.

Exemplary embodiments of inspecting primary filter 108 and/or secondary filter 110 can include visual inspection by either medical or non-medical personnel, inspecting by an electronic device or machine, or inspecting through mechanical means. Exemplary embodiments of inspecting by an electronic device or machine includes any type of device that is able to scan or image the primary filter 108 and/or secondary filter 110 such that the scanned or imaged picture of the primary filter 108 and/or secondary filter 110 can be digitally viewed or examined for imperfections such as rips or cuts that would impact the integrity of the sterilization cycle. Exemplary embodiments of mechanical inspection includes any type of inspection means that physically test that the integrity of the primary filter 108 and/or secondary filter 110 has been maintained.

It should be noted that exemplary embodiments of a sterilizing agent include any substance that provides for the destruction or elimination of living organisms, which often include heat, steam, pressure, gas, plasma, irradiation, chemical compounds, and chemical vapor.

Exemplary embodiments of this process provide that the first sealed interface is separate from the second sealed interface. Additionally, failure of the second sealed interface is independent of the first sealed interface. For example, if the second sealed interface fails and leaks sterilizing steam during a sterilization cycle, the first sealed interface should remain intact and should not be affected by the failure of the second sealed interface.

Figure 3A:
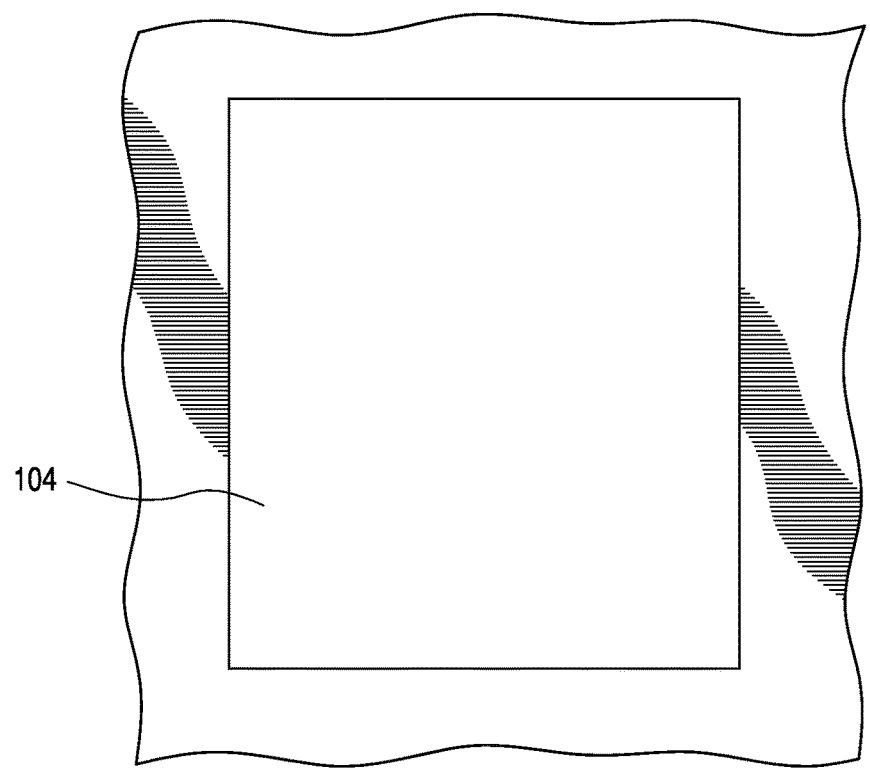
FIG. 3a is a top view of a vent of a sterilizing cabinet suitable for use in practicing exemplary embodiments of this invention.

Referring to FIG. 3a, a top view of an exemplary vent 104 is shown. Provided is a fenestrated surface with numerous openings that allow for the passage of a sterilizing agent, such as steam from sterilizing cabinet 100 during a sterilization cycle. It can be appreciated that FIG. 3a merely represents one embodiment of vent 104 and that exemplary embodiments of vent 104 include any arrangement of holes or openings that allow for the passage of a sterilizing agent.

Figure 3B:
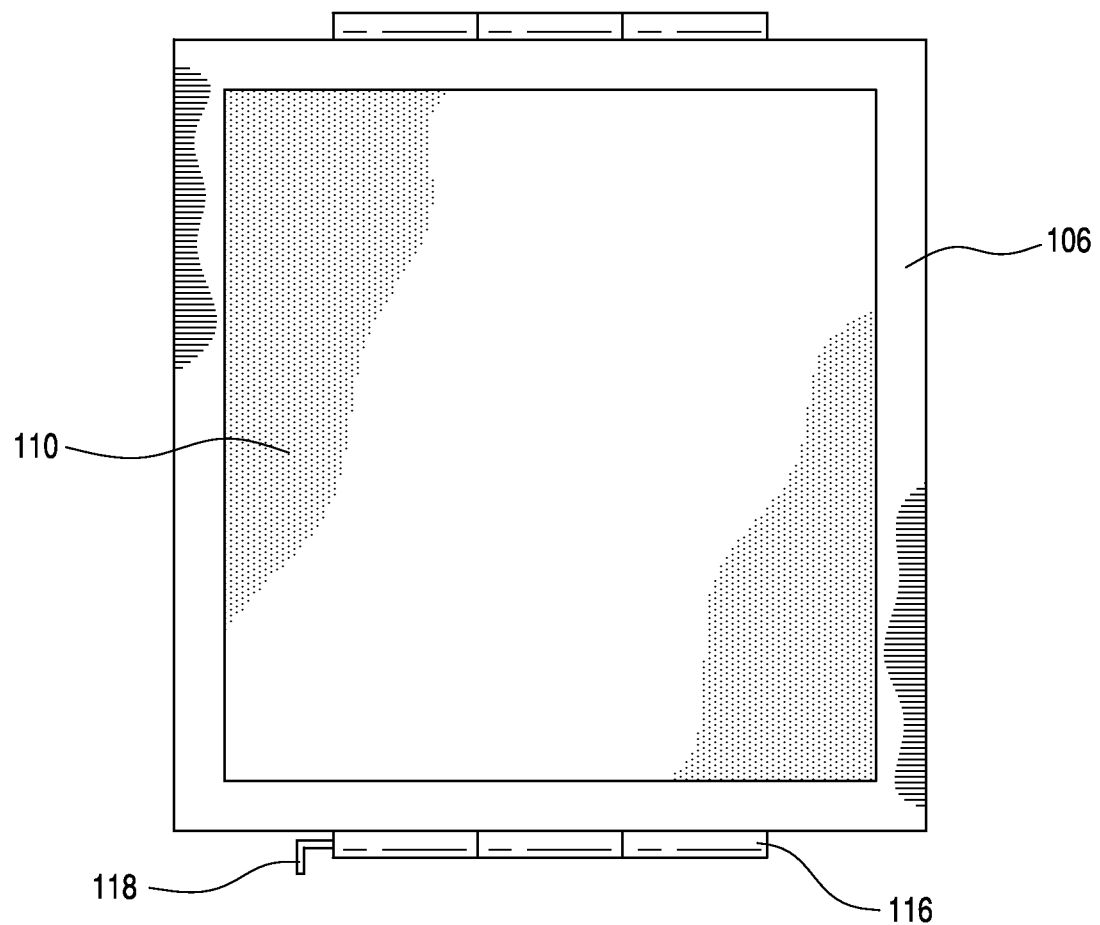
FIG. 3b is a perspective view of a filter arrangement of a sterilizing cabinet for use in practicing exemplary embodiments of this invention.

FIG. 3b provides a top view of a filtering arrangement covering vent 104. Shown in FIG. 3b is the top portion of secondary filter 110, filter holder 106 with hinges 116 and pin 118. Exemplary embodiments of this arrangement provide for a silicon seal between filter holder 106 and primary filter 108, between filter holder 106 and secondary filter 110 and sterilizing cabinet 100. This seal serves two primary purposes. First, it forces all of the sterilizing agent that enters and exits the sterilizing cabinet 100 to pass through the filters. Second, it keeps extraneous materials from entering the sterilizing cabinet 100 through vents 104, which are covered by primary filter 108 and secondary filter 110.

It can be appreciated that exemplary embodiments of the sealed interface between the primary filter 108 and the sterilizing cabinet 100 includes both direct contact between primary filter 108 and sterilizing cabinet 100 as well as indirect contact between primary filter 108 and sterilizing cabinet 100 through the use of a sealing agent, such as caulk or an adhesive. Likewise, the sealed interface between the secondary filter and the primary filter 108 or filter holder 106 includes both direct contact between primary filter 108 or filter holder 106 as well as indirect contact through the use of a sealing agent, such as caulk or an adhesive.

Figure 4A:
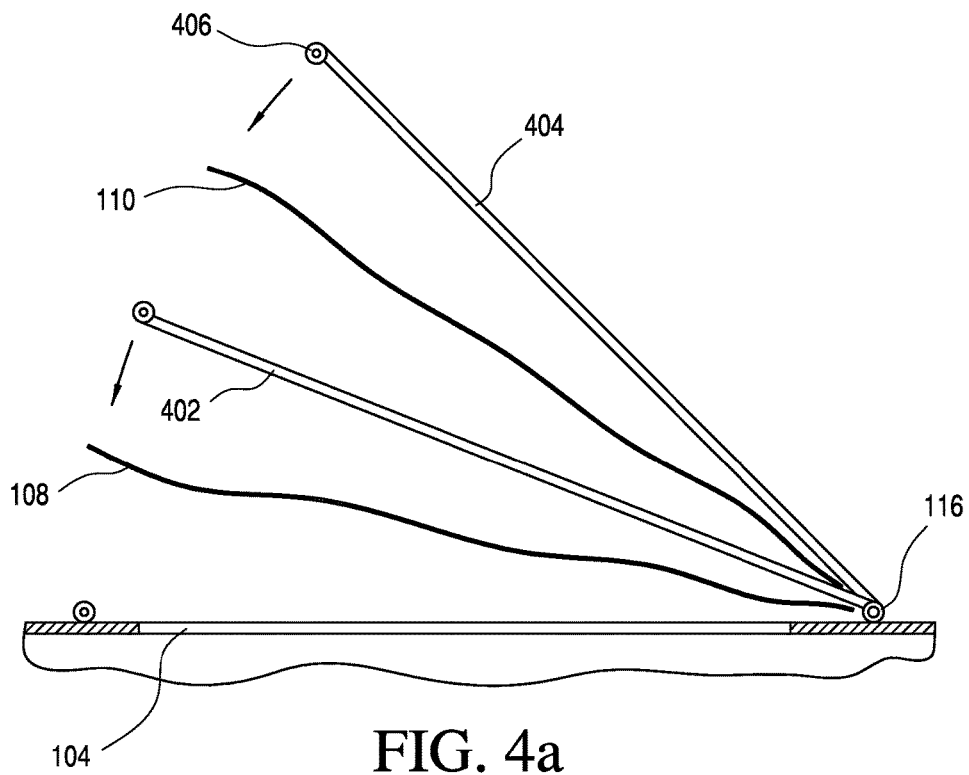
FIG. 4a is a perspective view of the movement of a filter arrangement of a sterilizing cabinet for use in practicing exemplary embodiments of this invention.

Referring to FIG. 4a, provided is a side view of the different elements and the type of movement allowed for filter holder 106 in exemplary embodiments of this invention. Shown in FIG. 4a is the outside face of sterilizing cabinet 100, vent 104, primary filter 108, secondary filter 110, hinge 116, filter holder 106 section 402 which secures primary filter 108, and filter holder 106 section 404 which secures secondary filter 110. In this exemplary embodiment sections 402 and 404 are able to rotate about hinge 116 and can be moved from the closed position (covering vent 104) to the open position (not covering vent 104) independent of each other. For instance section 404 can be moved to the open position while section 402 remains in the closed position. However, in order for section 402 to move to the open position, section 404 must also be in the open position since it overlays section 402. Also shown in FIG. 4a are holes 406 on section 402, section 404 and on sterilizing cabinet 100. When section 402 and 404 are in the closed position, the holes 406 line-up such that a pin 118 or locking key can be inserted through the holes 406. This prevents sections 402 and 404 from opening during a sterilization cycle or at any other time when opening would be undesirable.

In alternative exemplary embodiments sections 402 and 404 are maintained or locked in the closed position through the use of a clamp or latch. It can be appreciated that exemplary embodiments of these teachings provide for any mechanism that allows sections 402 and 404 of filter holder 106 to be maintained securely in the closed position and then opened when desired.

Figure 4B:
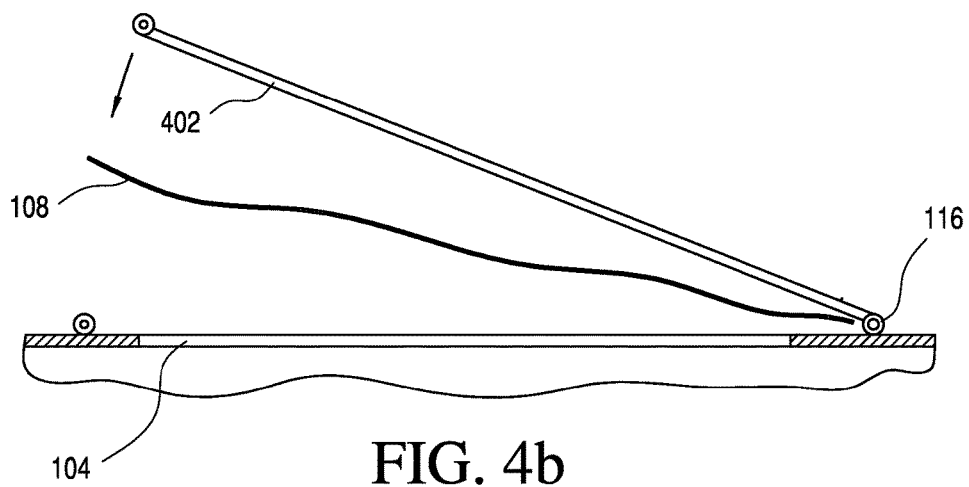
FIG. 4b is a perspective view of the movement of an alternative filter arrangement of a sterilizing cabinet for use in practicing exemplary embodiments of this invention.

FIG. 4b provides a perspective view of the movement of an alternative filter arrangement of a sterilizing cabinet for use in practicing exemplary embodiments of this invention. Shown in FIG. 4b is the outside face of sterilizing cabinet 100, vent 104, primary filter 108, hinge 116, and filter holder 106 section 402, which secures primary filter 108. It should be noted that in this exemplary embodiment, there is only one filter (i.e., primary filter 108) and one filter holder 106 section 402. Here, filter holder 106 section 402 is able to rotate about hinge 116. It can be moved from the closed position (covering vent 104) to the open position (not covering vent 104). Also shown in FIG. 4b are holes 406 on section 402. When section 402 is in the closed position, the holes 406 line-up such that a pin 118 or locking key can be inserted through the holes 406. This prevents section 402 from opening during a sterilization cycle or at any other time when opening would be undesirable.

Figure 5A:
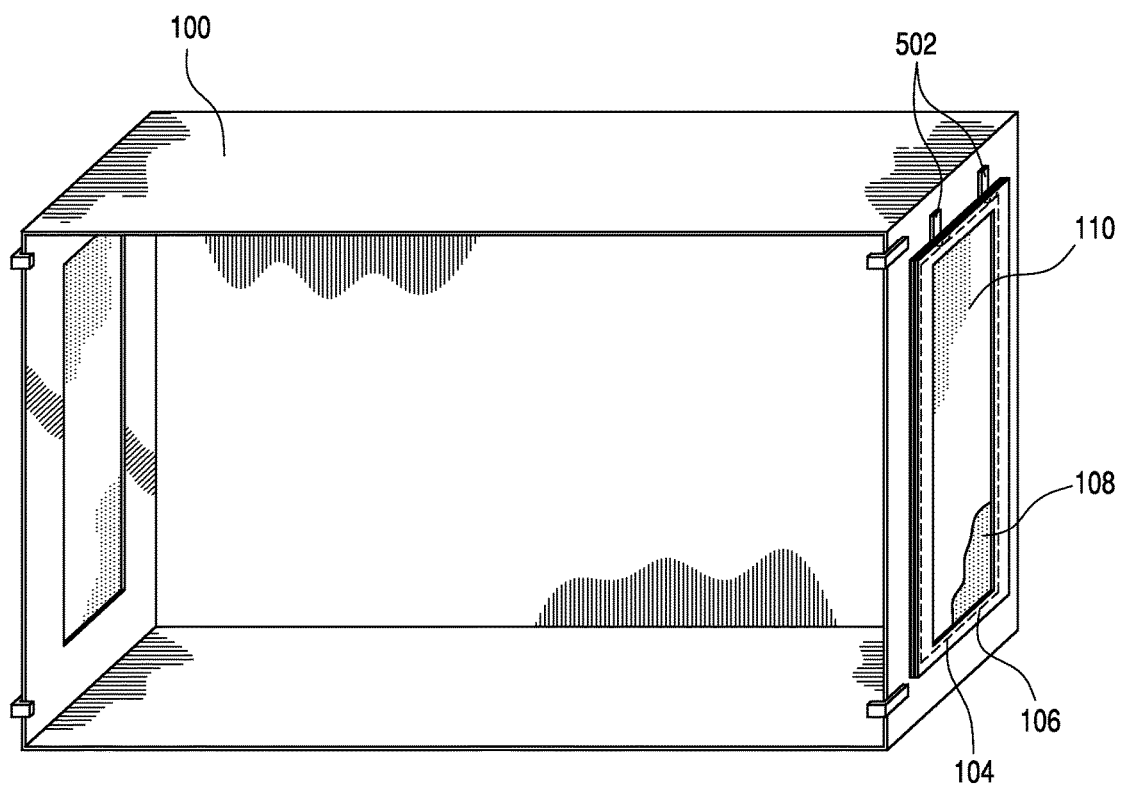
FIG. 5a is a perspective view of an alternative configuration of a sterilizing cabinet suitable for use in practicing exemplary embodiments of this invention.

In alternative exemplary embodiments, section 402 is maintained or locked in the closed position through the use of a clamp or latch. It can be appreciated that exemplary embodiments of these teachings provide for any mechanism that allows section 402 of filter holder 106 to be maintained securely in the closed position and then opened when desired FIG. 5a provides a perspective view of an alternative arrangement of sterilizing cabinet 100 with vents 104 on the sides of the cabinet. In this embodiment filter holders 110 are located on the sides of sterilizing cabinet 100 with primary filter 108 and secondary filter 110. Also shown in FIG. 5a are hangers 502 from which filter holder 106, primary filter 108 and secondary filter 110 attach to sterilizing cabinet 100. It can be appreciated that exemplary embodiments of sterilizing cabinet 100 include vents 104, primary filter 108, secondary filter 110 and filter holder 106 on the side of sterilizing cabinet 100.

Figure 5B:
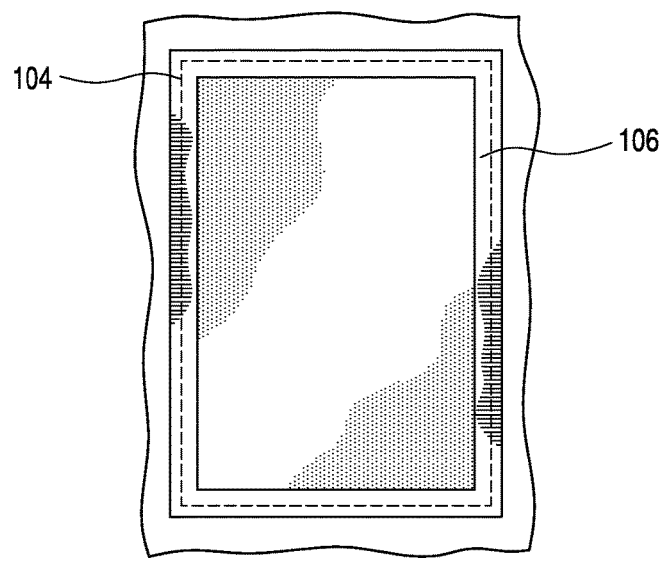
FIG. 5b is a perspective view of bottom section of a filter arrangement of a sterilizing cabinet suitable for use in practicing exemplary embodiments of this invention.
Figure 5C:
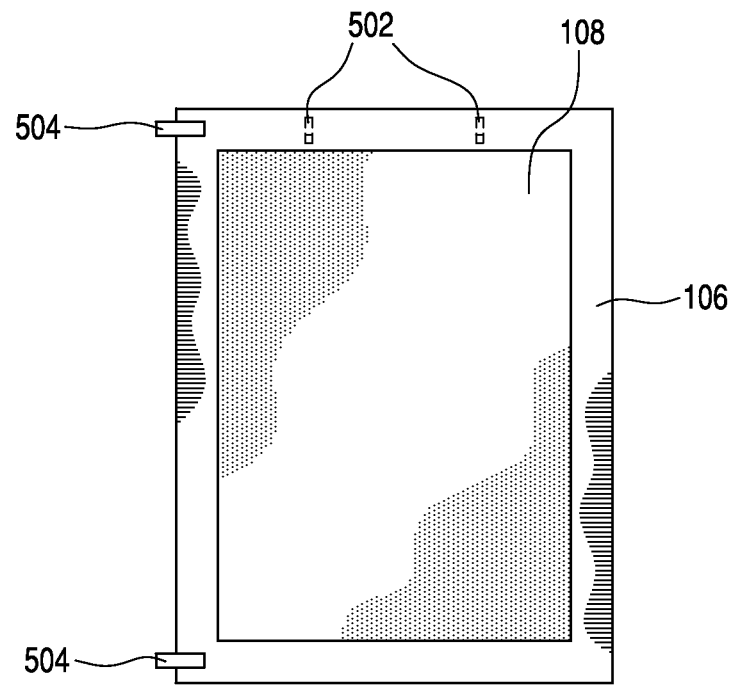
FIG. 5c is a perspective view of a middle section of a filter arrangement of a sterilizing cabinet suitable for use in practicing exemplary embodiments of this invention.

FIG. 5b shows a front facing view of vent 104 with filter holder 106 overlaying vent 104 on sterilizing cabinet 100. In this embodiment filter holder 106 is sized such its edges completely cover the portions surrounding vent 104. FIG. 5c shows primary filter 108 and filter holder 106 overlaying vent 104. Primary filter 108 as shown hangs from hangers 502 and attaches to filter holder 106 by clamps 504.

Figure 5D:
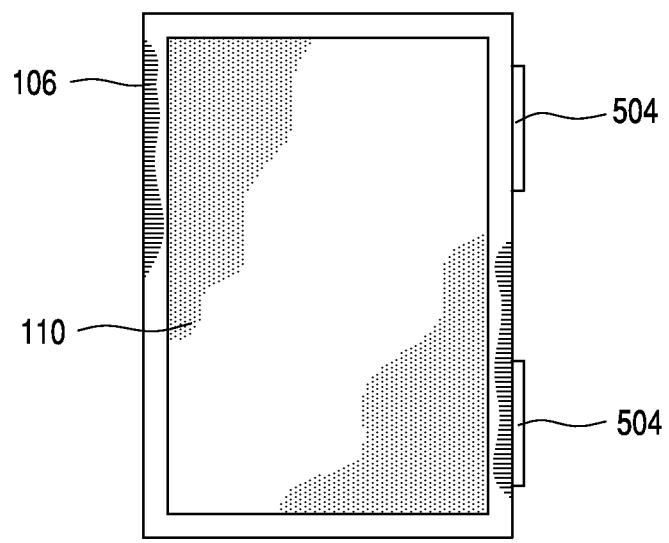
FIG. 5d is a perspective view of top section of a filter arrangement of a sterilizing cabinet suitable for use in practicing exemplary embodiments of this invention.

FIG. 5d shows secondary filter 110 in filter holder 106 overlaying primary filter 108 and vent 104. In this embodiment the portion of filter holder 106 which holds secondary filter 110 can be opened and closed through the use of hinged gasket 504 once pin 118 is removed from hole 406 maintaining the portion of filter holder 106 that holds secondary filter 110. This allows for secondary filter 110 to be removed from filter holder 106 while maintaining the position and seal of primary filter 108 over vent 104.

Figure 6A:
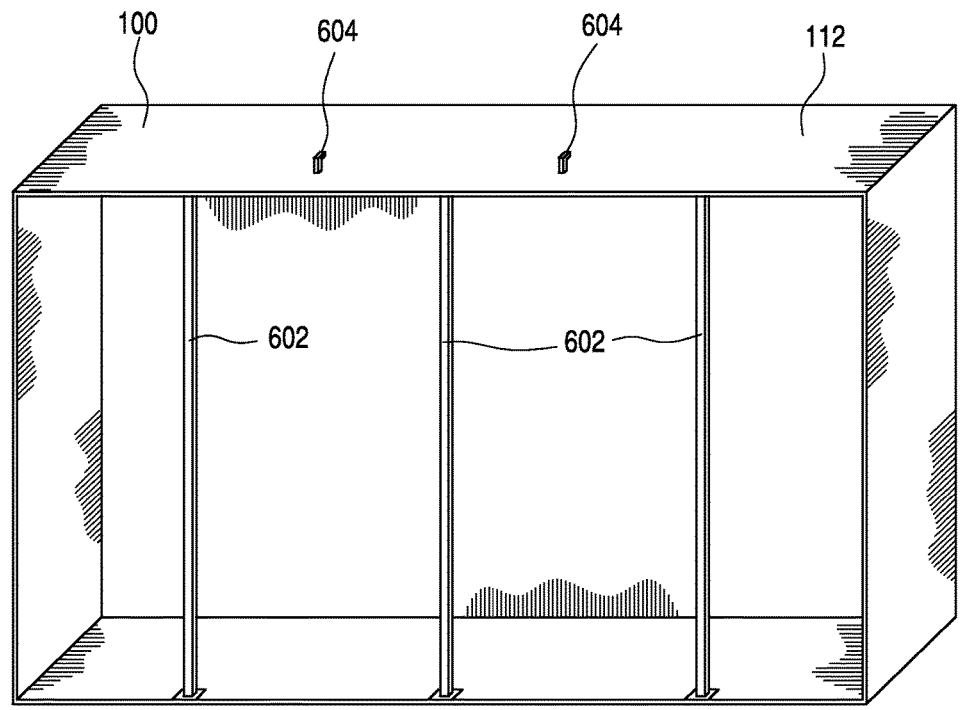
FIG. 6a is a perspective view of an alternative sterilizing cabinet suitable for use in practicing exemplary embodiments of this invention.
Figure 6B:
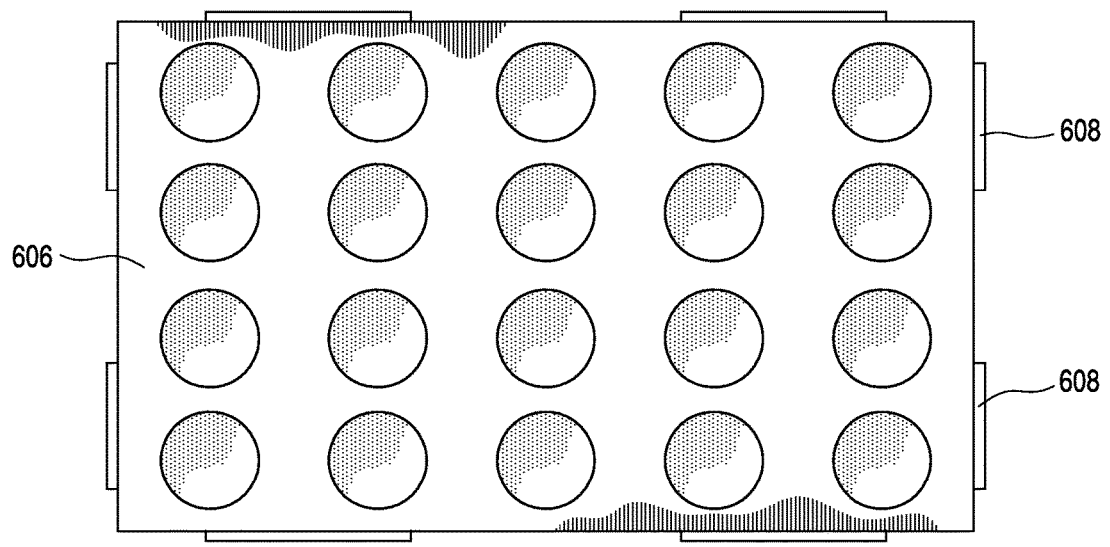
FIG. 6b is a front view of an alternative filter arrangement of a sterilizing cabinet suitable for use in practicing exemplary embodiments of this invention.

FIG. 6a provides a perspective view of an alternative sterilizing cabinet 100. Shown in FIG. 6a is sterilizing cabinet frame 112, bars 602 and hooks 604. In this embodiment there is no front side of sterilizing cabinet 100 in front of bars 602. It should be appreciated that exemplary embodiments of sterilizing cabinet 100 also include embodiments of sterilizing cabinet 100 that do not contain bars 602. In yet another exemplary embodiment of sterilizing cabinet 100, bars 602 are removeable such that bars 602 can be removeably affixed to sterilizing cabinet 100 when desired. FIG. 6b illustrates filter door 606 which contains primary filter 106. In exemplary embodiments filter door 606 covers the front opening of sterilizing cabinet 100 in FIG. 6a. Filter door 606 clamps onto sterilizing cabinet 100 with clamps 608. Bars 602 prevent the contents of sterilizing cabinet 100 (typically a tray containing instruments for sterilization) from ripping or breaking primary filter 108 and secondary filter 110.

Figure 6C:
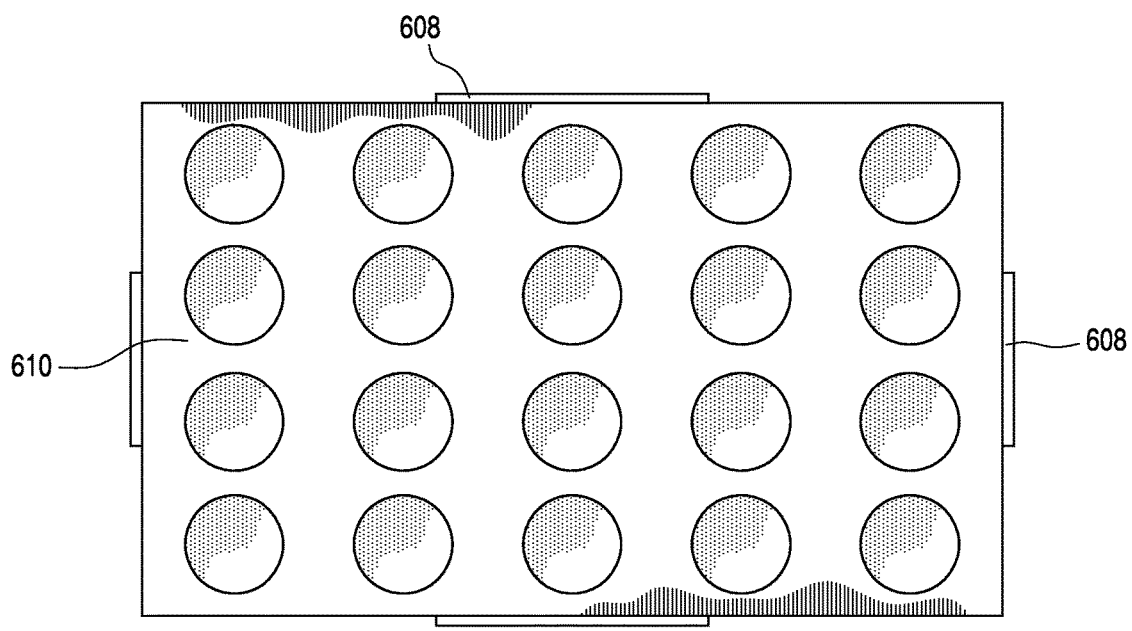
FIG. 6c is a front view of the top portion of an alternative filter arrangement of a sterilizing cabinet suitable for use in practicing exemplary embodiments of this invention.

FIG. 6c illustrates filter door 610 which attaches to filter door 606 and sterilizing cabinet 100 with the use of clamps 608. In this embodiment it can be appreciated that clamps 608 on filter door 610 fit into the spacing between clamps 608 on filter door 606. This arrangement prevents the clamps 608 from filter door 606 from interfering with clamps 608 from filter door 610. Additionally, since filter door 610 is attached independently from filter door 606, secondary filter 110 can be removed with filter door 610 after a sterilization cycle has completed without disturbing filter door's 606 seal with sterilizing cabinet 100. In this embodiment filter door 606 forms a seal with sterilizing cabinet 100 at the edges of the open portion of the sterilizing cabinet frame 112, such that any sterilizing steam that enters or exits sterilizing cabinet 100 during a sterilization cycle must pass through filter door 606 and primary filter 106. Likewise, filter door 610 forms a seal with filter door 606 such that any sterilizing steam that exits sterilizing cabinet 100 and primary filter 108 must pass through filter door 610 and secondary filter 110.

Figure 7A:
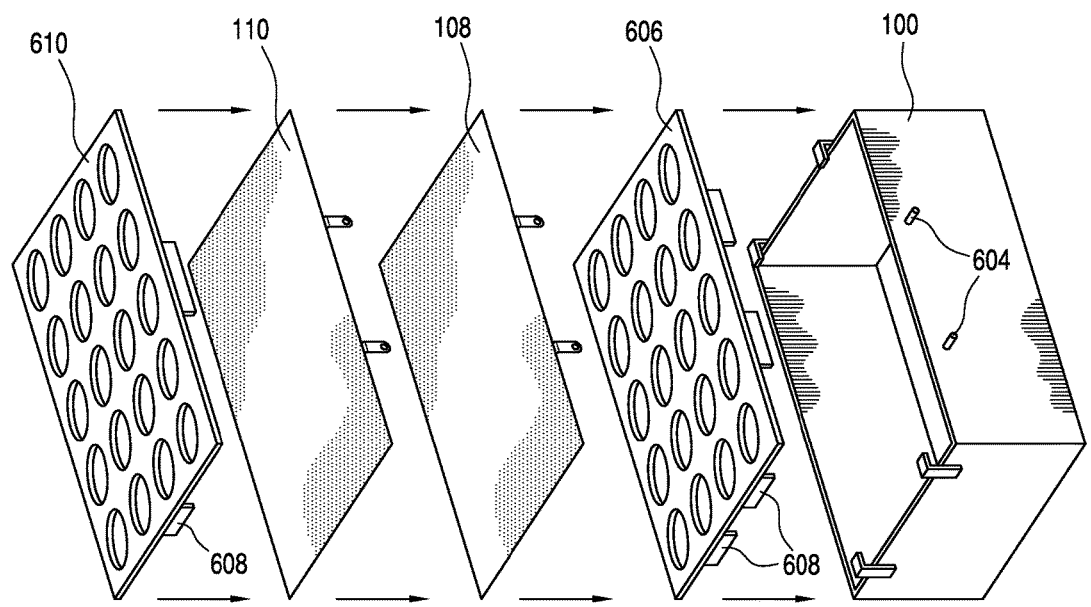
FIG. 7a is a perspective view of the separated elements of an alternative filter arrangement of a sterilizing cabinet suitable for use in practicing exemplary embodiments of this invention.

FIG. 7a depicts a perspective view of the construction of the alternative arrangement sterilizing cabinet 100 from FIGS. 6a, 6b and 6c. As shown filter door 606 with clamps 608 attach around the frame of sterilizing cabinet 100. Primary filter 108 is placed on top of filter door 606 and attaches to sterilizing cabinet 100 at hooks 604. Secondary filter 110 is placed on top of primary filter 108 and also attaches to sterilizing cabinet 100 at hooks 604. Filter door 610 is then placed on top of secondary filter 110 and attached to sterilizing cabinet 100 with clamps 608. As illustrated in FIG. 7a, exemplary embodiments of filter doors 606 and 608 contain numerous holes or openings along their surface, and allow for the passage of sterilizing steam. Exemplary embodiments of filter doors 606 and 608 are able to be fully or partially separable from sterilizing cabinet 100. It should also be appreciated that filter doors 606 and 608 can optionally employ the use of a hinge, clamp, clasp or the like as the mechanism for removing and replacing filter doors 606 and 608 on sterilizing cabinet 100.

Figure 7B:
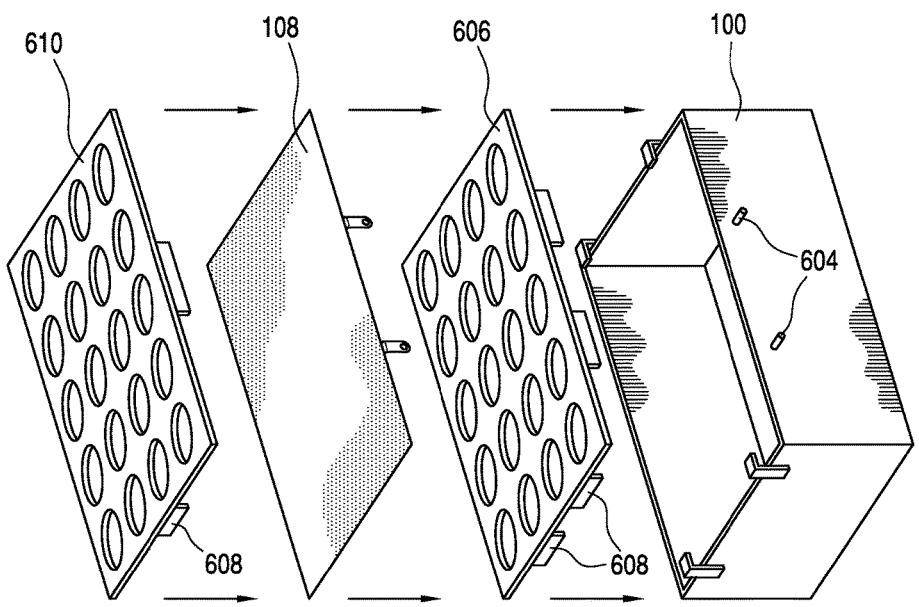
FIG. 7b is a perspective view of the separated elements of another filter arrangement of a sterilizing cabinet suitable for use in practicing exemplary embodiments of this invention.

FIG. 7b depicts an alternative perspective view of the construction of another alternative arrangement sterilizing cabinet 100. As shown filter door 606 with clamps 608 attach around the frame of sterilizing cabinet 100. Primary filter 108 is placed on top of filter door 606 and attaches to sterilizing cabinet 100 at hooks 604. In this embodiment, there is only a single filter and no secondary filter. Primary filter 108 creates a sealed interface with filter door 606 such that extraneous materials cannot enter sterilizing cabinet 100. Filter door 610 is then placed on top of primary filter 108 and attached to sterilizing cabinet 100 with clamps 608. In another exemplary embodiment, primary filter 108 does not create a sealed interface with filter door 606 until filter door 610 is placed on top of primary filter 108 and filter door 606. In this embodiment, a sealed interface between filter door 610 and primary filter 108, and a sealed interface between filter door 606 or sterilizing cabinet 100 and primary filter 108 is only created when filter door 610 is attached or affixed to sterilizing cabinet 100. As illustrated in FIG. 7b, exemplary embodiments of filter doors 606 and 608 which contain numerous holes or openings along their surface, which allow for the passage of sterilizing steam.

It should be noted that exemplary embodiments of FIG. 7b provide that filter door 610 can be removed from sterilizing cabinet 100, primary filter 108 and filter door 606 without disturbing or disrupting the sealed interface between primary filter 108 and filter door 606. This will prevent the possibility of extraneous materials from entering sterilizing cabinet 100 after a sterilizing cycle when filter door 610 is removed in order to either allow primary filter 108 and filter door 606 to be removed as well or for primary filter 108 to be inspected to verify that it maintained its integrity during the sterilizing cycle.

In an alternative exemplary embodiment, the sealed interface between filter door 610 and primary filter 108, and the sealed interface between filter door 606 or sterilizing cabinet 100 and primary filter 108 is broken or can be broken when filter door 610 is removed from sterilizing cabinet 100, primary filter 108, and filter door 606. In yet another exemplary embodiment, the sealed interface between filter door 610 and primary filter 108, and the sealed interface between filter door 606 or sterilizing cabinet 100 and primary filter 108 is only created and thereafter maintained when sterilizing cabinet 100 along with filter door 610, filter door 606 and primary filter 108 are exposed to a sterilization cycle. Exemplary embodiments of sterilizing cabinet 100 as depicted in FIG. 7b are able to maintain the sealed interface between filter door 610 and primary filter 108, and the sealed interface between filter door 606 or sterilizing cabinet 100 and primary filter 108 for an extended period of time following being exposed to a sterilization cycle, such as sterilizing steam. For example, the sealed interface may be able to remain intact for as long as 30-90 days. In other exemplary embodiments the sealed interface may only remain intact for a matter of hours.

Figure 8A:
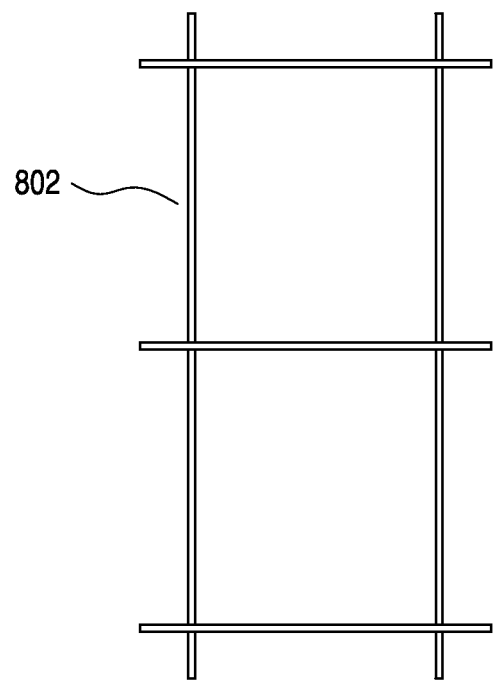
FIG. 8a is a top view of a spacer suitable for use in practicing exemplary embodiments of this invention.
Figure 8B:
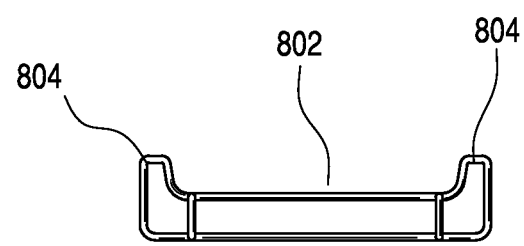
FIG. 8b is a side view of a spacer suitable for use in practicing exemplary embodiments of this invention.
Figure 8C:
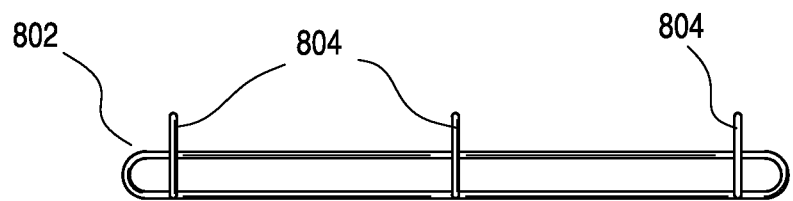
FIG. 8c is another side view of a spacer suitable for use in practicing exemplary embodiments of this invention.

Referring to FIGS. 8a, 8b and 8c, provided are different views of a spacer 802 for use in exemplary embodiments of sterilizing cabinet 100. In this embodiment spacer 802 has a wire frame and is sized such that when it is placed inside sterilizing cabinet 100 it does not move. The length and width of spacer 802 closely matches the dimensions (i.e., the depth and width) of the inside of sterilizing cabinet 100. This prevents spacer 802 from sliding or moving inside sterilizing cabinet 100 during a sterilization cycle or while sterilizing cabinet 100 is being moved. It should be appreciated that spacer 802 is shaped such that there are dividers or lips 804 along the edges of spacer 802 and at spacer's 802 midsection. The dividers or lips 804 are illustrated most clearly in FIGS. 8b and 8c. In practice, sterilizing trays can be placed on top of spacer 802 prior to a sterilization cycle. In order to ensure that all of the contents of sterilizing cabinet 100 are sterilized, it is advantageous to prevent sterilizing trays from touching. This can obscure portions of the sterilizing trays or their contents from the sterilizing steam. As such, the dividers or lips 804 provide a physical barrier between sterilizing trays creating a minimum separation between the trays. This allows the passage sterilizing steam during a sterilization cycle throughout sterilizing cabinet 100. Additionally, the dividers or lips 804 of spacer 802 are sized such that they accommodate the shape and size of sterilizing trays and thus substantially prevent lateral movement (e.g., sliding) of sterilizing trays when not desired before, during or following a sterilization cycle.

Figure 9A:
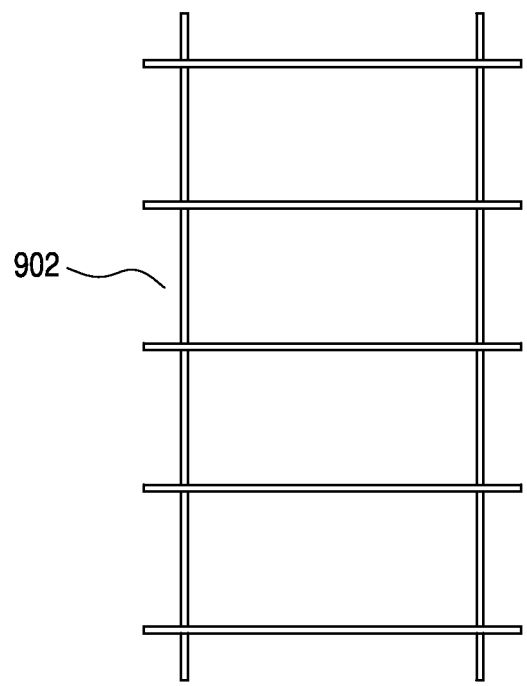
FIG. 9a is a top view of an alternative spacer suitable for use in practicing exemplary embodiments of this invention.
Figure 9B:
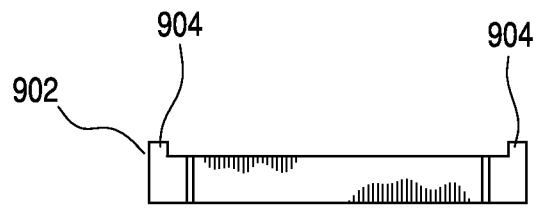
FIG. 9b is a side view of an alternative spacer suitable for use in practicing exemplary embodiments of this invention.
Figure 9C:
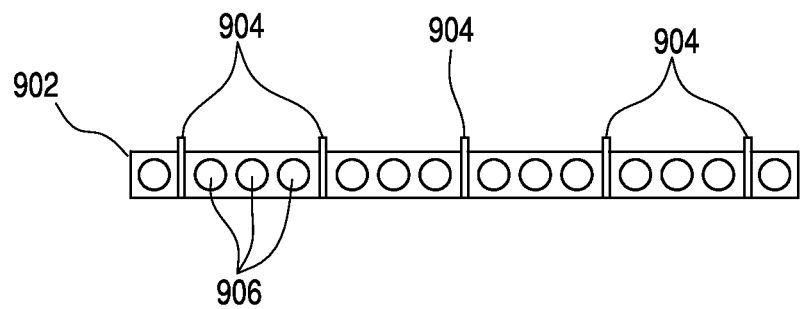
FIG. 9c is another side view of an alternative spacer suitable for use in practicing exemplary embodiments of this invention.

FIGS. 9a, 9b and 9c illustrate an alternative spacer 902 for use inside exemplary embodiments of sterilizing cabinet 100. In this embodiment spacer 902 is made of thin sheets (e.g., metal or aluminum alloys) with holes 906 throughout the length of the sheets. In this embodiment spacer 902 is sized such that when it is placed inside sterilizing cabinet 100 it does not move. The length and width of spacer 902 closely matches the dimensions (i.e., the depth and width) of the inside of sterilizing cabinet 100. This prevents spacer 902 from sliding or moving inside sterilizing cabinet 100 during a sterilization cycle or while sterilizing cabinet 100 is being moved. Spacer 902 is shaped such that there are dividers or lips 904 along the edges of spacer 902 and throughout spacer's 902 mid-section. The dividers or lips 904 can be viewed most clearly in FIGS. 9b and 9c. In practice, sterilizing trays can be placed on top of spacer 902 prior to a sterilization cycle. In order to ensure that all of the contents of sterilizing cabinet 100 are sterilized, it is advantageous to prevent sterilizing trays from touching. This can obscure portions of the sterilizing trays or their contents from the sterilizing steam. As such, the dividers or lips 904 provide a physical barrier between sterilizing trays creating a minimum separation between the trays. This allows the passage sterilizing steam during a sterilization cycle throughout sterilizing cabinet 100. Holes 906 encompasses any variation of openings that allow for the passage of sterilizing steam during a sterilization cycle yet maintaining structural integrity of spacer 902 to carry the weight of the sterilizing trays and their contents.

Exemplary embodiments of spacers 802 and 902 provide for the spacer to be fenestrated. In another exemplary embodiment spacers 802 and 902 are not reusable but are disposable and can only be sterilized once. In another exemplary embodiment spacers 802 and 902 provide vertical spacing between trays by at least 0.1 to 5 inches. In yet another exemplary embodiment, spacers 802 and 902 provide vertical spacing between trays by at least 10 to 26 inches.

Figure 10:
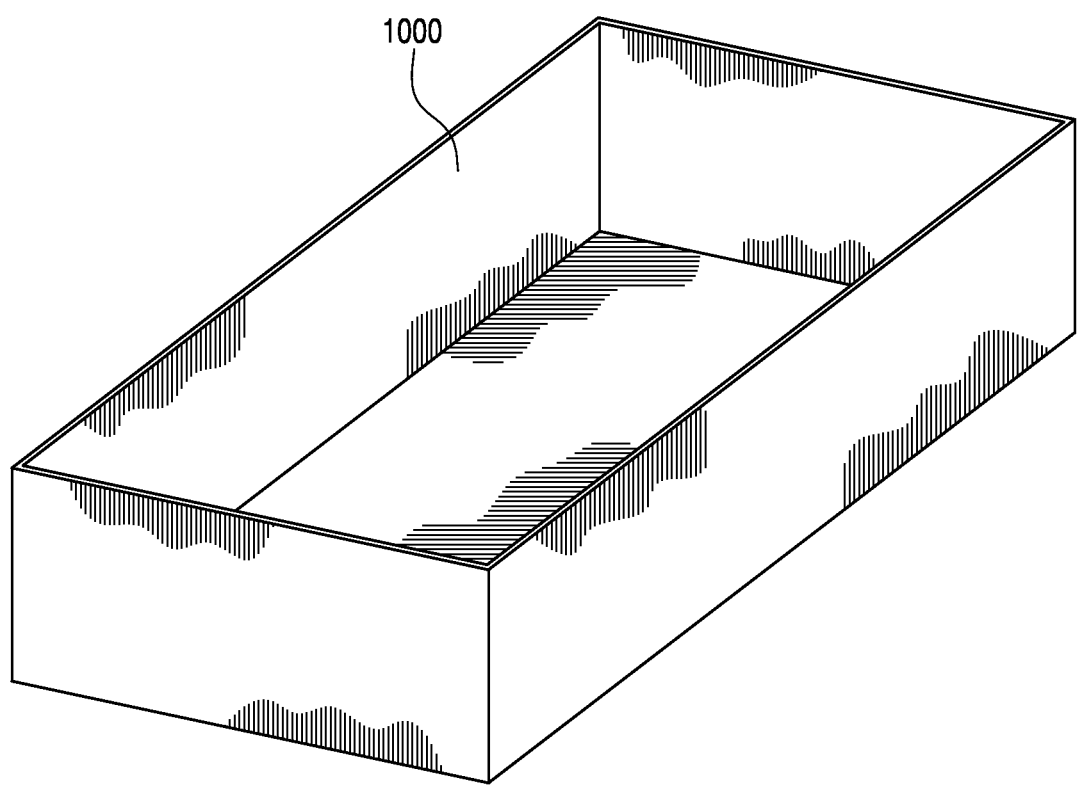
FIG. 10 is a perspective view of a sterilizing tray suitable for use in practicing exemplary embodiments of this invention.

FIG. 10 provides an exemplary embodiment of a sterilizing tray for practicing exemplary embodiments of this disclosure. For the purposes of this disclosure, the terms tray and pan are interchangeable and refer to an instrument with a closed rigid bottom and sides and an open top. Illustrated in FIG. 10 is sterilizing tray 1000 with an open top and a closed rigid bottom and sides. Sterilizing tray 1000 can be made of any material that can be sterilized (sterilizable) and is rigid enough such that it can hold items to be sterilized. For example sterilizing tray 1000 can be made of metals or metal alloys. Exemplary embodiments of sterilizing tray 1000 provide for a tray that has dimensions that make it suitable for use with spacers 802 and 902 and sterilizing cabinet 100. Exemplary embodiments of sterilizing tray 1000 also includes trays with holes, slits, fenestrations or other openings that allow for the passage of a sterilizing agent during a sterilization cycle.

In an exemplary embodiment in accordance of the present disclosure, spacers 802 or 902 can be used in conjunction with sterilizing cabinet 100 and one or more sterilizing trays 1000 during a sterilization cycle. In this embodiment the one or more sterilizing trays 1000 are of the shape and size so that they can be retained within sterilizing cabinet 100 and fit between the dividers 904 in spacers 902.

Figure 11:
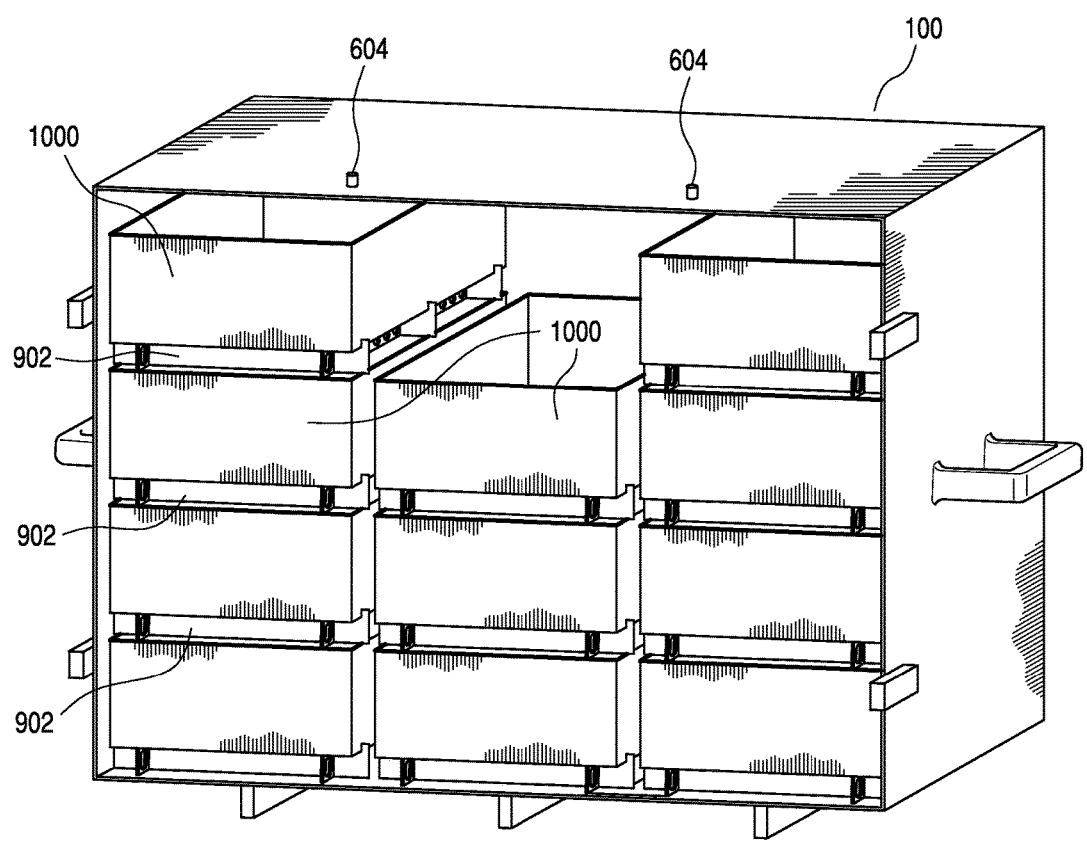
FIG. 11 is a perspective view of a sterilizing cabinet suitable for use in practicing exemplary embodiments of this invention.

In practice, as shown in FIG. 11, a first tray is placed in sterilizing cabinet 100 on a spacer 902. On top of the first tray 1000 spacer 902 is then placed. Next, a second tray 1000 is placed in sterilizing cabinet 100 on top of spacer 902. The spacer 902 vertically separates the first tray 1000 from the second tray 1000 in sterilizing cabinet 100. Spacer 902 also inhibits lateral displacement of the first and second tray 1000 through the use of the dividers and lips 904. The spacers 902 play the important role of allowing sterilizing steam to pass between the sterilizing trays 1000 during a sterilization cycle. It can be appreciated that exemplary embodiments include the addition of more sterilizing trays 1000 and spacers 902 arranged in accordance with the first and second sterilizing trays described. Exemplary embodiments of spacers 902 provide space between the first and second tray 1000 by at least 10 to 26 inches.

Figure 12:
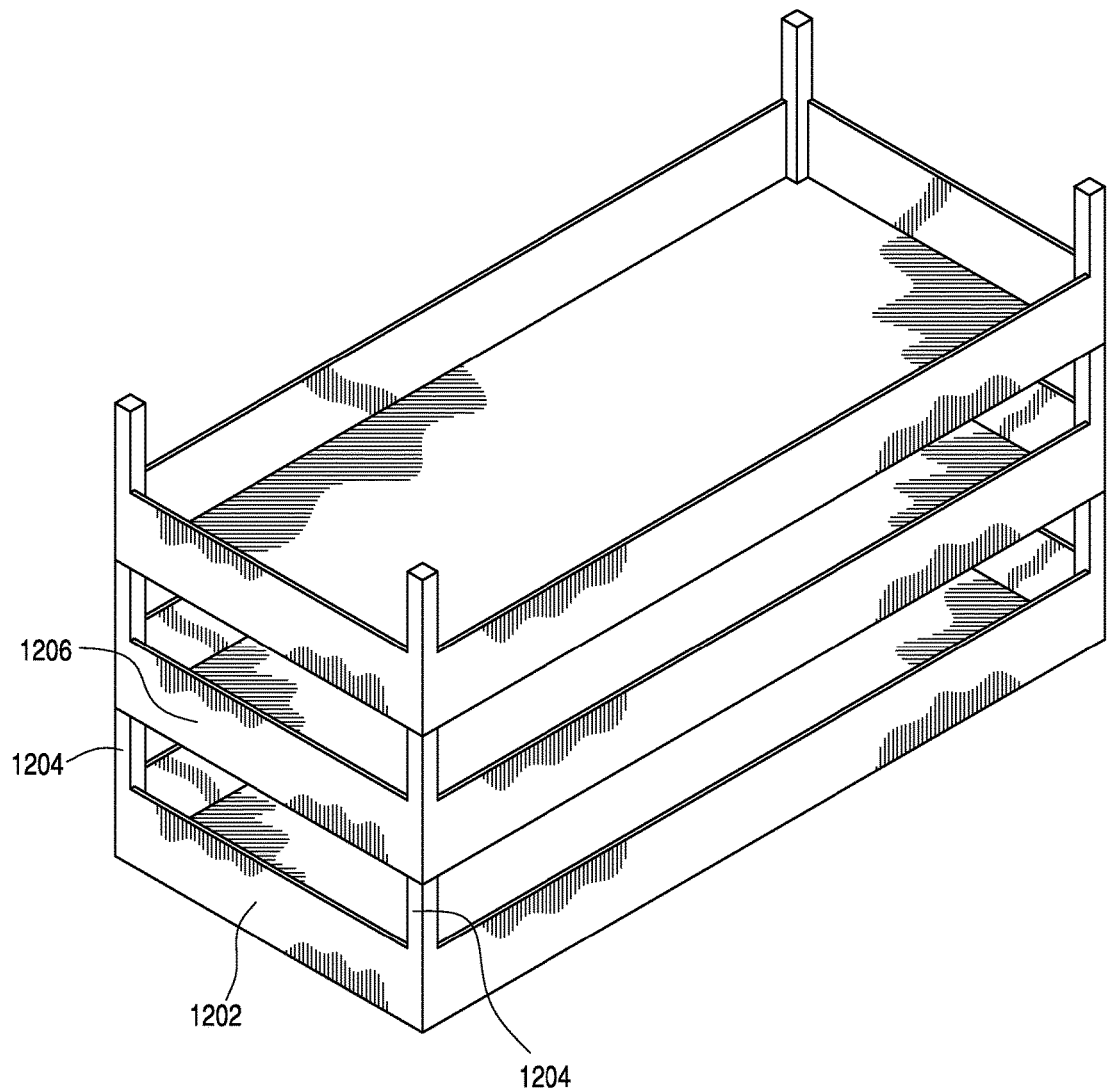
FIG. 12 is a perspective view of a pan assembly suitable for use in practicing exemplary embodiments of this invention.

Exemplary embodiments of these teachings also provide for a sterilizable pan assembly for sterilization within sterilizing cabinet 100. The sterilizable pan assembly as shown in FIG. 12 illustrates a first sterilizable pan 1202 with an open top and a closed bottom. Protruding from the top of the first sterilizable pan 1202 are four legs 1204. Exemplary embodiments of the first sterilizable pan 1202 also includes legs 1204 that protrude from the bottom of the first sterilizable pan 1202. These legs are configured to releaseably attach to a portion of a second sterilizable pan 1206. Legs 1204 when attached to the second sterilizable pan 1206 maintain a vertical spacing between the bottom of the first sterilizable pan 1202 and the top of the second sterilizable pan 1206. In one exemplary embodiment the vertical spacing is at least 0.1 to 5 inches. In another exemplary embodiment, the vertical spacing is such that it allows for the passage of a sterilizing steam from a sterilization cycle of sterilizing cabinet 100. Exemplary embodiments of this pan assembly are configured such that they can be used within sterilizing cabinet 100 during a sterilization cycle.

Figure 13A:
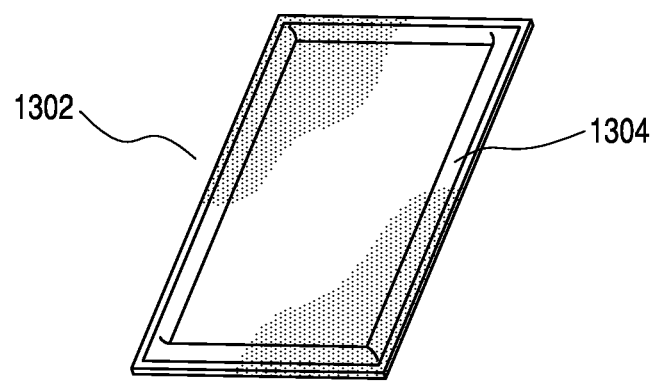
FIG. 13a is a perspective view of a filter suitable for use in practicing exemplary embodiments of this invention.
Figure 13B:
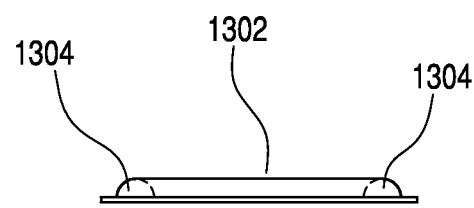
FIG. 13b is a side view of a filter suitable for use in practicing exemplary embodiments of this invention.

Referring to FIG. 13a, provided is an exemplary embodiment of a filter suitable for use in practicing exemplary embodiments of this disclosure. Shown in FIG. 13a is filter 1302 with a beaded edge 1304. Filter 1302 can be made of any type of porous paper or cellulose type material. In other embodiments, filter 1302 is made of polymeric substances, such as polypropylene. Filter 1302 is required to be both porous and dense enough to allow the passage of a sterilizing agent, such as steam, through its membrane, but also resilient enough to not rip or tear during a sterilizing cycle or during insertion/clamping into a filter holder. In another embodiment, filter 1302 is both porous and less resilient such that filter 1302 can be ripped or torn during use in a sterilizing cycle or with filter holder 106. The beaded edge 1304 creates a raised portion along the edges of the filter 1302 as shown in FIG. 13b. This enables filter 1302 to create a sealed interface when used with sterilizing cabinet 100 and filter holder 106 over vents 104. In an alternative embodiment, beaded edge 1304 is placed inside the edge of filter 1302 rather than on the edge of filter 1302 such that there is a space between the edge of filter 1302 and beaded edge 1304.

Exemplary embodiments of filter 1302 provide for filter 1302 to have different densities along given cross-sections of the face of filter 1302. For instance, filter 1302 may have a higher density along its periphery and a lower density towards its center. Exemplary embodiments of filter 1302 also provide for filter 1302 to have different thicknesses throughout its cross-section. The different thicknesses of filter 1302 provide different lengths of travel for sterilizing agents, which pass through filter 1302.

Exemplary embodiments of filter 1302 have a length and width that corresponds to the size of vents 104 of sterilizing cabinet 100 and filter holder 106. Additionally, the thickness of beaded edge 1304 corresponds to a size that is able to fit between sterilizing cabinet 100 and filter holder 106 or between the different sections of filter holder 106. The thickness of beaded edge 1304 is also such that the sealed interface between sterilizing cabinet 100 and filter holder 106 or between the different sections of filter holder 106 prevents extraneous materials from entering sterilizing cabinet 100 and forces all of the sterilizing agent that enters and exits sterilizing cabinet 100 to pass through filter 1302.

The beaded edge 1304 can be made of a silicone based material or any other material that can create a sealed interface between sterilizing cabinet 100 or filter holder 106 and filter 1302. The beaded edge 1304 also is required to be able to withstand high temperatures in excess of 275 degrees without compromising its structural or chemical integrity. Exemplary embodiments of filter 1502 have a length and width that corresponds to the size of vents 104 of sterilizing cabinet 100 and filter holder 106.

Figure 14A:
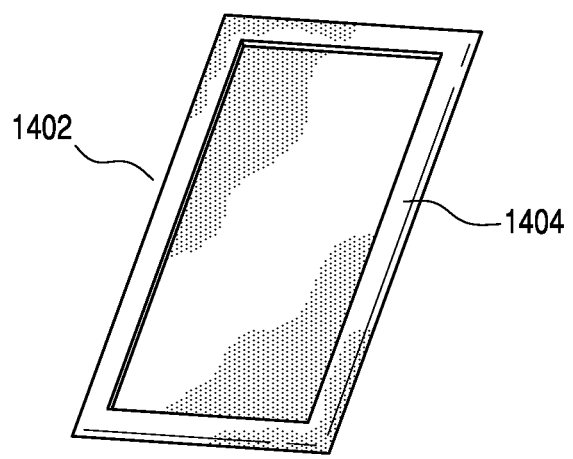
FIG. 14a is a perspective view of an alternative filter suitable for use in practicing exemplary embodiments of this invention.

FIG. 14a provides an alternative exemplary embodiment of a filter suitable for use in practicing exemplary embodiments of this disclosure. Shown in FIG. 14a is filter 1402 with folded edge 1404. Filter 1402 can be made of any type of porous paper or cellulose type material. In other embodiments filter 1402 is made of polymeric substances, such as polypropylene. Filter 1402 is required to be porous enough to allow the passage of a sterilizing agent, such as steam through its membrane, but also resilient enough to not rip or tear during a sterilizing cycle or during insertion/clamping into a filter holder 106. In another embodiment filter 1402 is both porous and less resilient such that filter 1402 can be ripped or torn during use in a sterilizing cycle or with filter holder 106.

Figure 14B:
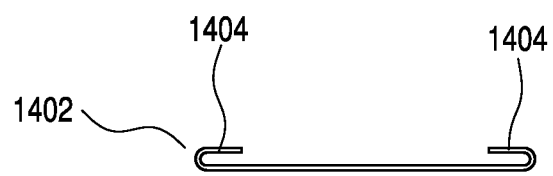
FIG. 14b is a side view of an alternative filter suitable for use in practicing exemplary embodiments of this invention.

The folded edge 1404 is created by the edges of filter 1402 folded onto itself thereby creating a thicker membrane along the edges of filter 1402 as shown in FIG. 14b. The thicker membrane of folded edge 1404 provides for a better-sealed interface between sterilizing cabinet 100 and filter holder 106 as there is less likelihood that spaces can be created between filter 1402 and sterilizing cabinet 100 which would allow for the passage of sterilizing steam or extraneous materials. Exemplary embodiments of filter 1402 have a length and width that corresponds to the size of vents 104 of sterilizing cabinet 100 and filter holder 106.

Additionally, the thickness of folded edge 1404 corresponds to a size that is able to fit between sterilizing cabinet 100 and filter holder 106 or between the different sections of filter holder 106. The thickness of edge 1404 is also such that the sealed interface between sterilizing cabinet 100 and filter holder 106 or between the different sections of filter holder 106 prevents extraneous materials from entering sterilizing cabinet 100 and forces all of the sterilizing agent that enters and exits sterilizing cabinet 100 to pass through filter 1402.

Figure 15A:
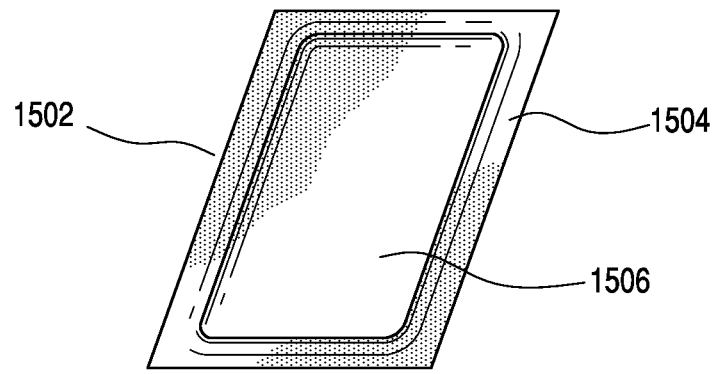
FIG. 15a is a perspective view of another filter suitable for use in practicing exemplary embodiments of this invention.

Referring to FIG. 15a, provided is another exemplary embodiment of a filter suitable for use in exemplary embodiments of this disclosure. Shown in FIG. 15a is filter 1502, filter edge 1504 and filter center 1506. Filter 1502 can be made of any type of porous paper or cellulose type material. In other embodiments filter 1502 is made of polymeric substances, such as polypropylene. Filter 1502 is required to be porous enough to allow the passage of a sterilizing agent, such as steam through its membrane, but also resilient enough to not rip or tear during a sterilizing cycle or during insertion/clamping into a filter holder 106. In another embodiment filter 1502 is both porous and less resilient such that filter 1502 can be ripped or torn during use in a sterilizing cycle or with filter holder 106.

Figure 15B:
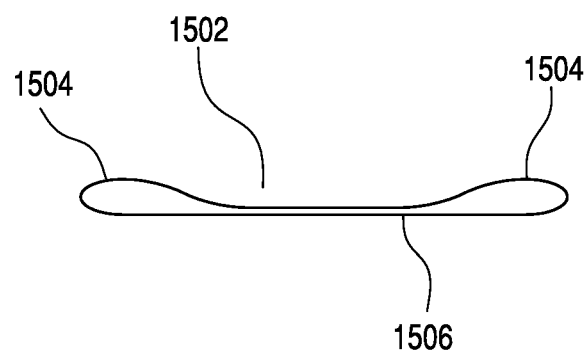
FIG. 15b is a side view of another filter suitable for use in practicing exemplary embodiments of this invention.

Filter edge 1504 provides for a thicker portion of filter 1502 as shown in FIG. 15b. The thickness of filter edge 1504 enables filter 1502 to make a better compressed sealed interface with sterilizing cabinet 100 and filter holder 106. Exemplary embodiments of filter 1502 have a length and width that corresponds to the size of vents 104 of sterilizing cabinet 100 and filter holder 106. Additionally, the thickness of edge 1504 corresponds to a size that is able to fit between sterilizing cabinet 100 and filter holder 106 or between the different sections of filter holder 106. The thickness of edge 1504 is also such that the sealed interface between sterilizing cabinet 100 and filter holder 106 or between the different sections of filter holder 106 prevents extraneous materials from entering sterilizing cabinet 100 and forces all of the sterilizing agent that exits sterilizing cabinet 100 to pass through center 1506 of filter 1502.

Center 1506 of filter 1502 includes all of the area of filter 1502 other than edge 1504 that is of normal or customary thickness for a filter that allows the passage of sterilizing steam, but prevents the passage of other extraneous materials.

Figure 16:
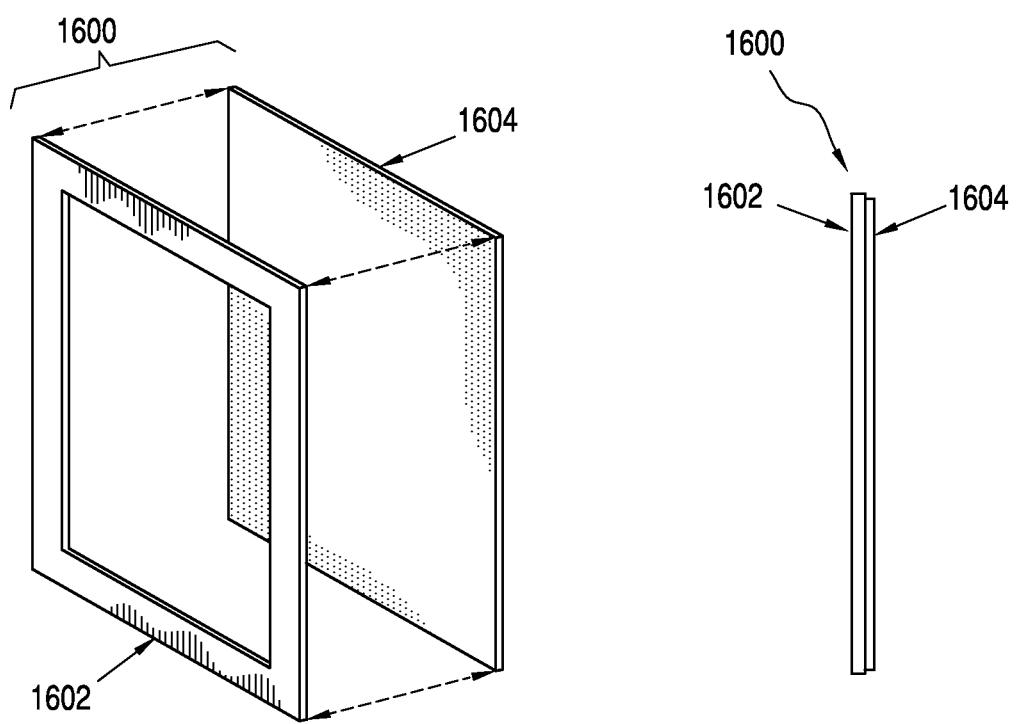
FIG. 16 is a perspective view of a filter cartridge suitable for use in practicing exemplary embodiments of this invention.

Shown in FIG. 16 is an exemplary filter cartridge 1600 suitable for use in practicing exemplary embodiments of this disclosure. FIG. 16 includes a separated view and a side view of filter cartridge 1600 in which the different elements have been separated. Filter cartridge 1600 includes a frame 1602 and filter 1604. Frame 1602 provides a substantially rigid frame that is substantially resistant from ripping or tearing. Frame 1602 is typically made out of a cardboard or like material. Frame 1602 can be made out of any type of material that is both substantially rigid and is able to maintain its integrity during and after undergoing a sterilization cycle. Exemplary embodiments of frame 1602 can be made out of polymer based materials or cellulose based materials. In other exemplary embodiments, frame 1602 is flexible and less rigid and may become deformed or shrink during a sterilization cycle. In another exemplary embodiment, frame 1602 can be made out of any type of material that is both flexible, less rigid and is able to maintain its integrity during and after undergoing a sterilization cycle. In one exemplary embodiment, frame 1602 is composed of medical grade light board. In another exemplary embodiment, frame 1602 is composed of a silicone material. Filter 1604 can be made of any type of porous paper or cellulose type material. In other embodiments filter 1604 is made of polymeric substances, such as polypropylene. Filter 1604 is required to be porous enough to allow the passage of a sterilizing agent, such as steam through its membrane, but also resilient enough to not rip or tear during a sterilizing cycle. Exemplary embodiments of filter cartridge 1600 are able to provide sufficient integrity to form a sealed interface with a confronting surface, such as a sterilizing cabinet and/or a filter door or doors, and is able to maintain its integrity during and after undergoing a sterilization cycle.

Exemplary embodiments of filter cartridge 1600 provide that frame 1602 and filter 1604 are removeably coupled to each other through the use of an adhesive. In another exemplary embodiment frame 1602 and filter 1604 are not removeably coupled, but are permanently affixed to one another or are integral with one another. In yet another exemplary embodiment, frame 1602 and filter 1604 are removeably coupled to each other through the use of an intermediary adhesive, such as double sided tape or the like. Exemplary adhesives are able to create a sealed interface between frame 1602 and filter 1604 and maintain the sealed interface between frame 1602 and filter 1604 prior to, during and following a sterilization cycle. One exemplary adhesive suitable for use in filter cartridge 1600 is that found is U.S. Pat. No. 3,691,140. Exemplary adhesives between frame 1602 and filter 1604 create a seal between frame 1602 and filter 1604 such that extraneous materials are not able to pass between the sealed interface of frame 1602 and filter 1604. Exemplary adhesives between frame 1602 and filter 1604 allow for filter 1604 to be removeable when desired, typically after undergoing sterilizing cycle, such that substantially all of filter 1604 can be removed in a single piece. That is, the adhesive and materials of frame 1602 and filter 1604 are selected to provide for non-destructive separation of frame 1602 and filter 1604.

Figure 17:
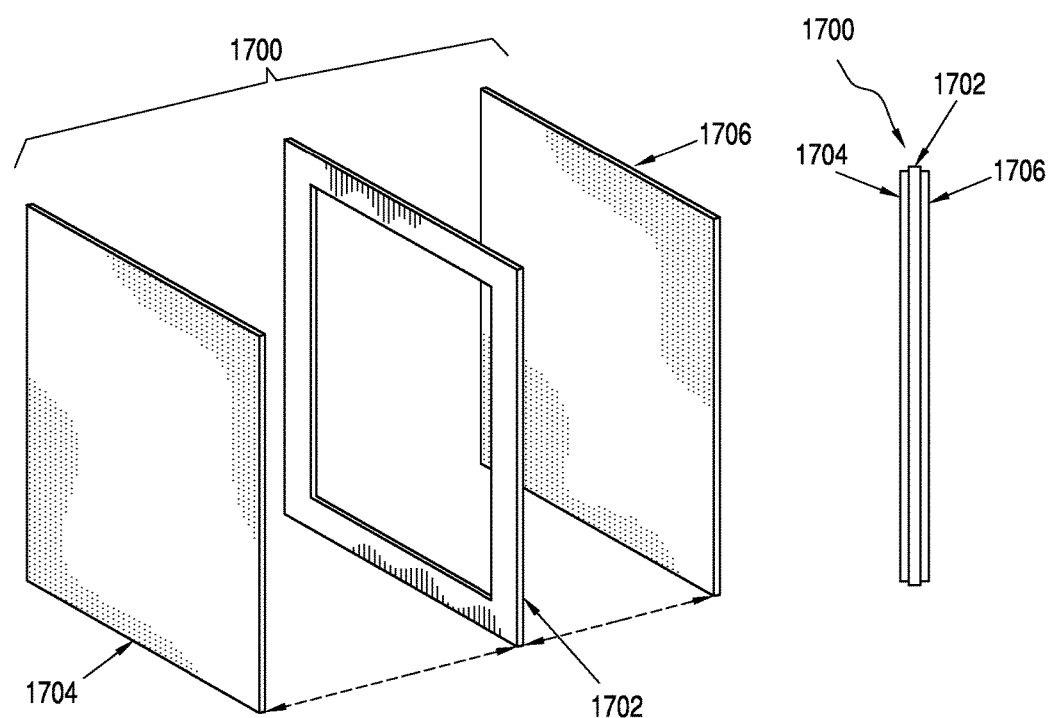
FIG. 17 is a perspective view of an alternative filter cartridge suitable in practicing exemplary embodiments of this invention.

Referring to FIG. 17, illustrated is filter cartridge 1700 suitable to use in practicing exemplary embodiments of this disclosure. FIG. 17 includes a separated view and a side view of filter cartridge 1700 in which the different elements have been separated. Filter cartridge 1700 includes a frame 1702, filter 1704, and filter 1706. Frame 1702 provides a substantially rigid frame that is substantially resistant from ripping or tearing. In other exemplary embodiments, frame 1702 is flexible and less rigid and may become deformed or shrink during a sterilization cycle. Frame 1702 is typically made out of a cardboard or like material. Frame 1702 can be made out of any type of material that is both rigid and is able to maintain its integrity during and after undergoing a sterilization cycle. Exemplary embodiments of frame 1702 can be made out of polymer based materials or cellulose based materials. In another exemplary embodiment, frame 1702 can be made out of any type of material that is flexible, less rigid and is able to maintain its integrity during and after undergoing a sterilization cycle. In one exemplary embodiment, frame 1702 is composed of medical grade light board. In another exemplary embodiment, frame 1702 is composed of a silicone material.

Filter 1704 and filter 1706 can be made of any type of porous paper or cellulose type material. In other embodiments, filter 1704 and filter 1706 are made of polymeric substances, such as polypropylene. Filter 1704 and filter 1706 are required to be porous enough to allow the passage of a sterilizing agent, such as steam through its membrane, but also resilient enough to not rip or tear during a sterilizing cycle. Exemplary embodiments of filter cartridge 1700 are able to provide sufficient integrity to form a sealed interface with a confronting surface, such as a sterilizing cabinet and/or a filter door or doors, and is able to maintain its integrity during and after undergoing a sterilization cycle.

Exemplary embodiments of filter cartridge 1700 provide that frame 1702, is removeably coupled to filter 1704 and filter 1706 through the use of an adhesive. In another exemplary embodiment frame 1702, filter 1704, and filter 1706 are not removeably coupled, but are permanently affixed to one another or are integral with one another. In yet another exemplary embodiment, frame 1702 is removeably coupled to filter 1704 and filter 1706 through the use of an intermediary adhesive, such as double sided tape or the like. As shown in FIG. 17, filter 1704 and filter 1706 are removeably coupled to frame 1702 such that they are located on opposing sides of frame 1702. Exemplary adhesives are able to create a sealed interface between frame 1702 and filter 1704, and between frame 1702 and filter 1706. One exemplary adhesive suitable for use in filter cartridge 1700 is that found is U.S. Pat. No. 3,691,140. Exemplary adhesives are also able to maintain the sealed interface between frame 1702 and filter 1704 prior to, during and following a sterilization cycle, and between frame 1702 and filter 1706 prior to, during and following a sterilization cycle. Exemplary adhesives between frame 1702 and filter 1704 and between frame 1702 and filter 1706 create a seal between frame 1702 and filter 1704, and between frame 1702 and filter 1706 such that extraneous materials are not able to pass between frame 1702 and filter 1704 or between frame 1702 and filter 1706. Exemplary adhesives between frame 1702 and filter 1704, and between frame 1702 and filter 1706 allow for filter 1604 and filter 1706 to be removeable from frame 1702 when desired, typically after undergoing sterilizing cycle, such that substantially all of filter 1704 and filter 1706 can be removed in a single piece.

Figure 18:
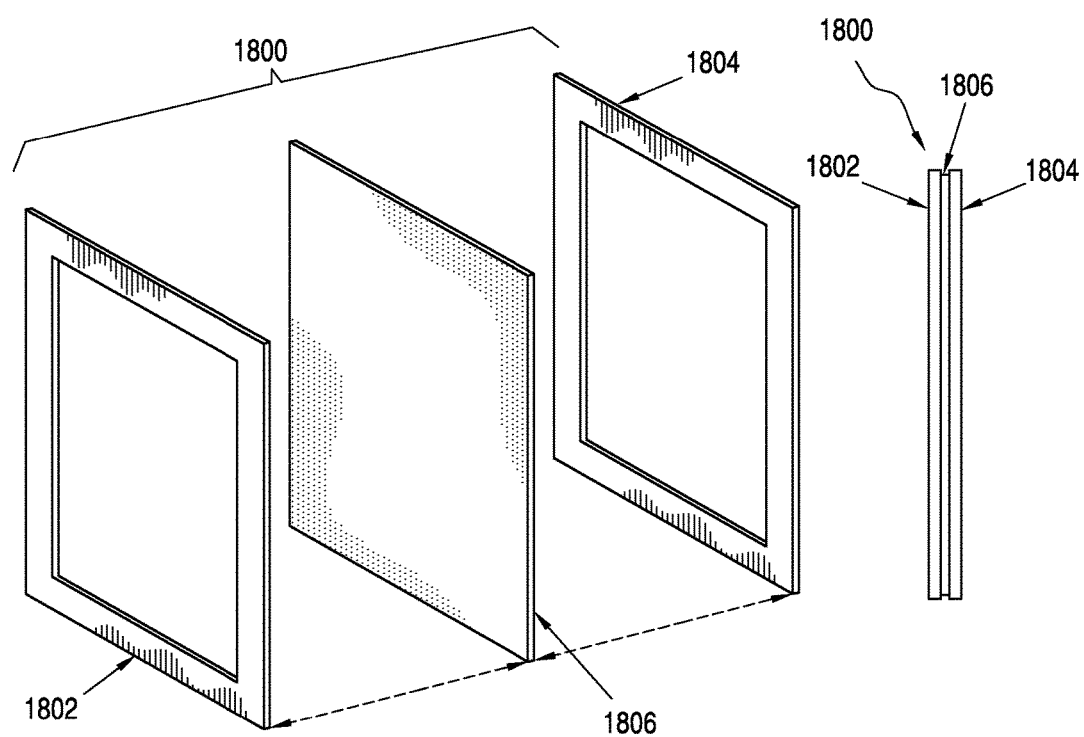
FIG. 18 is a perspective view of an alternative filter cartridge suitable in practicing exemplary embodiments of this invention.

Referring to FIG. 18, shown is an exemplary filter cartridge 1800 suitable for use in practicing exemplary embodiments of this disclosure. FIG. 18 includes a separated view and a side view of filter cartridge 1800 in which the different elements have been separated. Filter cartridge 1800 includes a frame 1802, frame 1804 and filter 1806. Frames 1802 and 1804 provide a substantially rigid frame that is substantially resistant from ripping or tearing. Frames 1802 and 1804 are typically made out of a cardboard or like material. Frames 1802 and 1804 can be made out of any type of material that is both substantially rigid and is able to maintain its integrity during and after undergoing a sterilization cycle. Exemplary embodiments of frames 1802 and 1804 can be made out of polymer based materials or cellulose based materials. In other exemplary embodiments, frames 1802 and 1804 are flexible and less rigid and may become deformed or shrink during a sterilization cycle. In another exemplary embodiment, frames 1802 and 1804 can be made out of any type of material that is flexible, less rigid and is able to maintain its integrity during and after undergoing a sterilization cycle. In one exemplary embodiment, frames 1802 and 1804 are composed of medical grade light board. In another exemplary embodiment, frames 1802 and 1804 are composed of a silicone material. Filter 1806 can be made of any type of porous paper or cellulose type material. In other embodiments filter 1806 is made of polymeric substances, such as polypropylene. Filter 1806 is required to be porous enough to allow the passage of a sterilizing agent, such as steam through its membrane, but also resilient enough to not rip or tear during a sterilizing cycle. Exemplary embodiments of filter cartridge 1800 are able to provide sufficient integrity to form a sealed interface with a confronting surface, such as a sterilizing cabinet and/or a filter door or doors, and is able to maintain its integrity during and after undergoing a sterilization cycle.

Exemplary embodiments of filter cartridge 1800 provide that frames 1802 and 1804 are removeably coupled to filter 1806 through the use of an adhesive. In another exemplary embodiment frames 1802 and 1804, and filter 1806 are not removeably coupled, but are permanently affixed to one another or are integral with one another. In yet another exemplary embodiment, frames 1802 and 1804 are removeably coupled to filter 1806 through the use of an intermediary adhesive, such as double sided tape or the like. Exemplary adhesives are able to create a sealed interface between frame 1802 and filter 1806, and between 1804 and filter 1806 and maintain the sealed interface between frame 1802 and filter 1806, and between frame 1804 and filter 1806 prior to, during and following a sterilization cycle. One exemplary adhesive suitable for use in filter cartridge 1800 is that found is U.S. Pat. No. 3,691,140. Exemplary adhesives create a seal between frame 1802 and filter 1806, and between frame 1804 and filter 1806 such that extraneous materials do not pass between frame 1802 and filter 1806, or between frame 1804 and filter 1806. Exemplary adhesives between frame 1802 and filter 1806, and between frame 1804 and filter 1806 allow for filter 1806 to be removeable when desired, typically after undergoing sterilizing cycle, such that substantially all of filter 1806 can be removed in a single piece.

Figure 19:
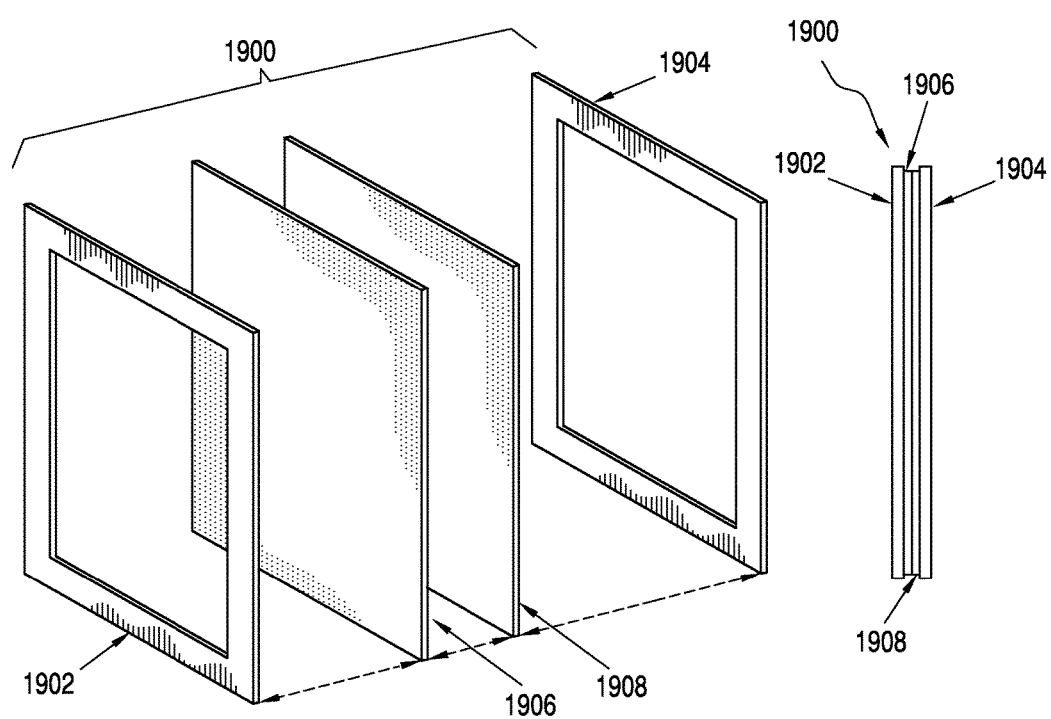
FIG. 19 is a perspective view of another filter cartridge suitable in practicing exemplary embodiments of this invention.

Referring to FIG. 19, shown is an exemplary filter cartridge 1900 suitable for use in practicing exemplary embodiments of this disclosure. FIG. 19 includes a separated view and a side view of filter cartridge 1900 in which the different elements have been separated. Filter cartridge 1900 includes a frame 1902, frame 1904, filter 1906 and filter 1908. Frames 1902 and 1904 provide a substantially rigid frame that is substantially resistant from ripping or tearing. Frames 1902 and 1904 are typically made out of a cardboard or like material. Frames 1902 and 1904 can be made out of any type of material that is both substantially rigid and is able to maintain its integrity during and after undergoing a sterilization cycle. In other exemplary embodiments, frames 1902 and 1904 are flexible and less rigid and may become deformed or shrink during a sterilization cycle. Exemplary embodiments of frames 1902 and 1904 can be made out of polymer based materials or cellulose based materials. In another exemplary embodiment, Frame 1902 and 1904 can be made out of any type of material that is flexible, less rigid and is able to maintain its integrity during and after undergoing a sterilization cycle. In one exemplary embodiment, frames 1902 and 1904 are composed of medical grade light board. In another exemplary embodiment, frames 1902 and 1904 are composed of a silicone material. Filters 1906 and 1908 can be made of any type of porous paper or cellulose type material. In other embodiments filters 1906 and 1908 are made of polymeric substances, such as polypropylene. Filters 1906 and 1908 are required to be porous enough to allow the passage of a sterilizing agent, such as steam through its membrane, but also resilient enough to not rip or tear during a sterilizing cycle. Exemplary embodiments of filter cartridge 1900 are able to provide sufficient integrity to form a sealed interface with a confronting surface, such as a sterilizing cabinet and/or a filter door or doors, and is able to maintain its integrity during and after undergoing a sterilization cycle.

Exemplary embodiments of filter cartridge 1900 provide that frames 1902 and 1904 are removeably coupled to filters 1906 and 1908 through the use of an adhesive. In another exemplary embodiment frames 1902 and 1904, and filters 1906 and 1908 are not removeably coupled, but are permanently affixed to one another or are integral with one another. In yet another exemplary embodiment, frames 1902 and 1904 are removeably coupled to filters 1906 and 1908 through the use of an intermediary adhesive, such as double sided tape or the like. Exemplary adhesives are able to create a sealed interface between frame 1902 and filter 1906, between frame 1904 and filter 1906, between frame 1904 and filter 1908 and also maintain the sealed interface between frames 1902 and 1904, and filters 1906 and 1908 prior to, during and following a sterilization cycle. One exemplary adhesive suitable for use in filter cartridge 1900 is that found is U.S. Pat. No. 3,691,140. Exemplary adhesives between frames 1902 and 1904, and filters 1906 and 1908 create a seal between frames 1902 and 1904, and filter 1906 and 1908 such that extraneous materials do not pass between frames 1902 and 1904, and filters 1906 and 1908. Exemplary adhesives between frames 1902 and 1904, and filters 1906 and 1908 allow for filters 1906 and 1908 to be removeable from frames 1902 and 1904 when desired, typically after undergoing sterilizing cycle, such that substantially all of filters 1906 or 1908 can be removed in a single piece.

Figure 20:
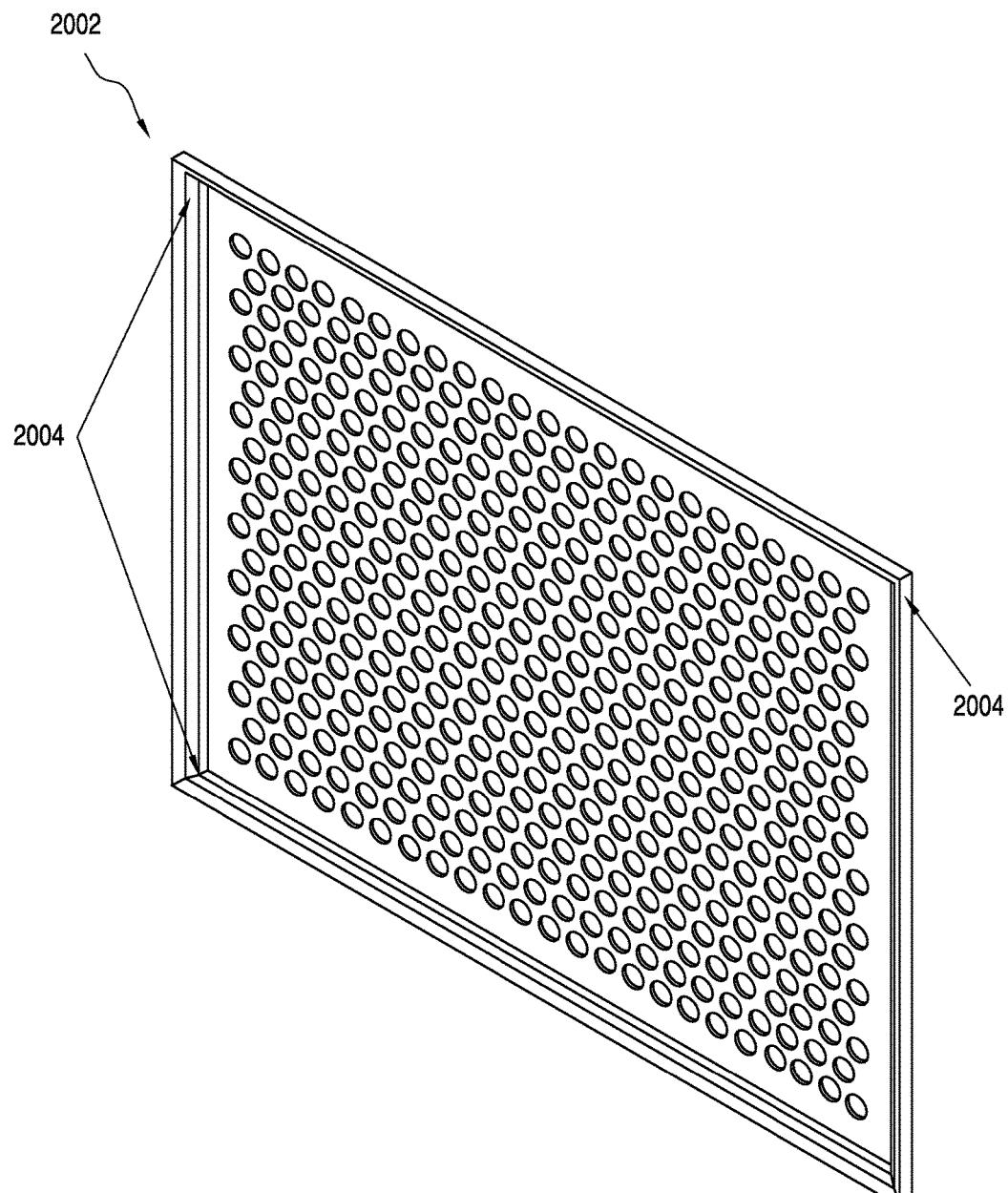
FIG. 20 is a filter cartridge holder suitable in practicing exemplary embodiments of this invention.

Referring to FIG. 20, shown is an exemplary filter door for a filter cartridge suitable for use in practicing exemplary embodiments of this disclosure. Shown in FIG. 20 is an exemplary outer filter door 2002. Filter door 2002 includes tabs or catches 2004, which protrude perpendicular from the back face of filter door 2002. Filter door 2002 as illustrated in FIG. 20 contains numerous holes or openings along its surface, which allow for the passage of sterilizing steam. In the embodiment depicted in FIG. 20, the tabs or catches 2004 are located in each of the four corners of filter door 2002. However, it should be noted that in other exemplary embodiments there can be more or less than four tabs or catches 2004. Additionally, tabs or catches 2004 can be located in different arrangements. Exemplary tabs or catches 2004 provide a mechanism for removeably locating or placing a filter cartridge on filter door 2002, such that a filter cartridge can be placed between tabs or catches 2004 and is in contact with tabs or catches 2004 without bending, folding or otherwise compromising the integrity of a filter cartridge.

Figure 21:
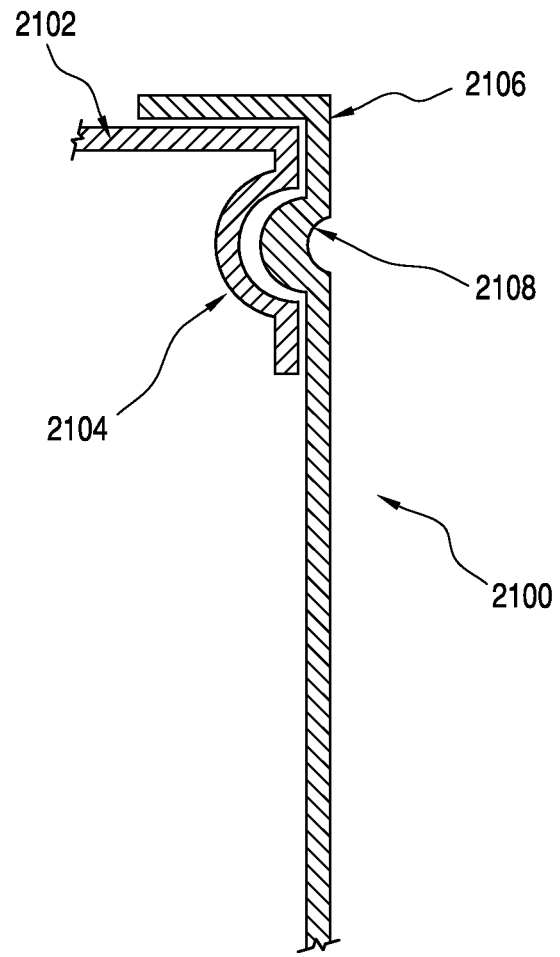
FIG. 21 is a magnified cross-sectional view of sterilizing cabinet and a filter door suitable for use in practicing exemplary embodiments of this disclosure.

Referring to FIG. 21, shown is a magnified cross-sectional view of an exemplary sterilizing cabinet and filter door suitable for use in practicing exemplary embodiments of this disclosure. Shown in FIG. 21 is a cross-sectional view of sterilizing cabinet 2102 with trough section 2104, and filter door 2106 with trough section 2108. Exemplary embodiments of trough section 2104 and trough section 2106 run along the entire edge of sterilizing cabinet 2102 and filter door 2106. Trough section 2104 and trough section 2106 are shaped such that a sealed interface is maintained throughout the trough (i.e., between trough section 2104 and trough section 2106) when a single filter, multiple filters, or a filter cartridge is placed between trough section 2104 and trough section 2106. Exemplary embodiments of trough section 2104 and trough section 2106 have a size and depth such that the movement of extraneous materials through the sealed interface between sterilizing cabinet 2102 and filter door 2106 is substantially prevented. In practice, a filter cartridge may be placed and compressed between the sterilizing cabinet 2102 and filter door 2106 such that the filter cartridge is deformed into the shape of the trough in which it is compressed.

Figure 22:
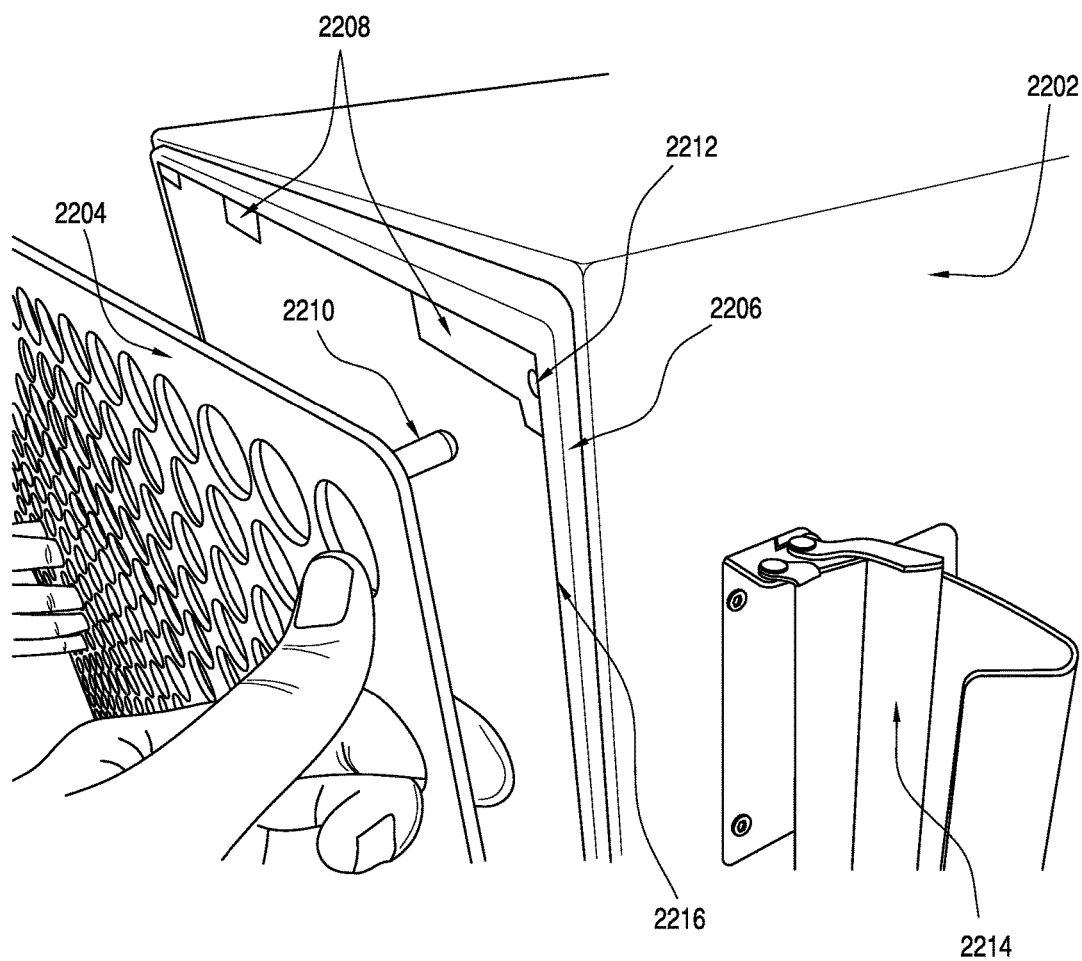
FIG. 22 is a perspective view of an exemplary sterilizing cabinet and filter door suitable for use in practicing exemplary embodiments of the present disclosure.

Referring to FIG. 22, shown is a perspective view of an exemplary sterilizing cabinet and filter door suitable for use in practicing exemplary embodiments of the present disclosure. Illustrated in FIG. 22 is sterilizing cabinet 2202, filter door 2204, trough section 2206, sterilizing cabinet tab 2208, filter door pin 2210, pin hole 2212, and clamp 2214. Exemplary embodiments of filter door pin 2210 are located on the top two corners of filter door 2204. In other exemplary embodiments, filter door pins 2210 are located at all four corners of filter door 2204. Filter door pins 2210 are of the size and shape to fit within pin hole 2212. Exemplary embodiments of filter door pin 2210 and pin hole 2212 are located such that filter door 2204 properly aligns and covers the open front of sterilizing cabinet 2202. Exemplary embodiments of filter door pin 2210 and pin hole 2212 maintain filter door 2204 is a loosely attached position to sterilizing cabinet 2202.

In other exemplary embodiments, filter door 2204 with filter door pin 2210 aligns with pin holes 2212 on sterilizing cabinet 2202 such that there is a small gap between the edge 2216 of sterilizing cabinet 2202 and filter door 2204. It can be appreciated that pin hole 2212 is located on sterilizing cabinet tab 2208. Exemplary embodiments of sterilizing cabinet tab 2208 are located at least in the four corners of sterilizing cabinet 2202 along edge 2216. In other exemplary embodiments, a sterilizing cabinet tab 2208 is also located within the middle of the vertical and horizontal edge 2216 of sterilizing cabinet 2202 such that there are eight (8) sterilizing cabinet tabs 2208. In another exemplary embodiment sterilizing cabinet 2202 includes one or more sterilizing cabinet tab 2208. Exemplary embodiments of sterilizing cabinet tab 2208 overlap with filter door 2204 when placed over the front opening of sterilizing cabinet 2202 such that filter door 2204 is prevented from falling or moving into the interior of sterilizing cabinet 2202 when filter door 2204 is aligned with pin hole 2212.

FIG. 22 also shows clamp 2214. Exemplary embodiments of clamp 2214 are located on the vertical sides of sterilizing cabinet 2202. However, exemplary embodiments of clamp 2214 can be placed in many different arrangements along the sides of sterilizing cabinet 2202 such that clamps 2214 are able to clasp and maintain filter door 2204 in a sealed position over the open front of sterilizing cabinet 2202. Exemplary embodiments of clamps 2214 are able to clasp and release filter door 2204 and an outer filter door from sterilizing cabinet 2202. Exemplary embodiments of clamp 2214 are sized such that a sealed interface is created between sterilizing cabinet 2202, a filter or filters, and the filter doors. The sealed interface prevents the passage of extraneous materials between the filter doors and sterilizing cabinet 2202.

Figure 23:
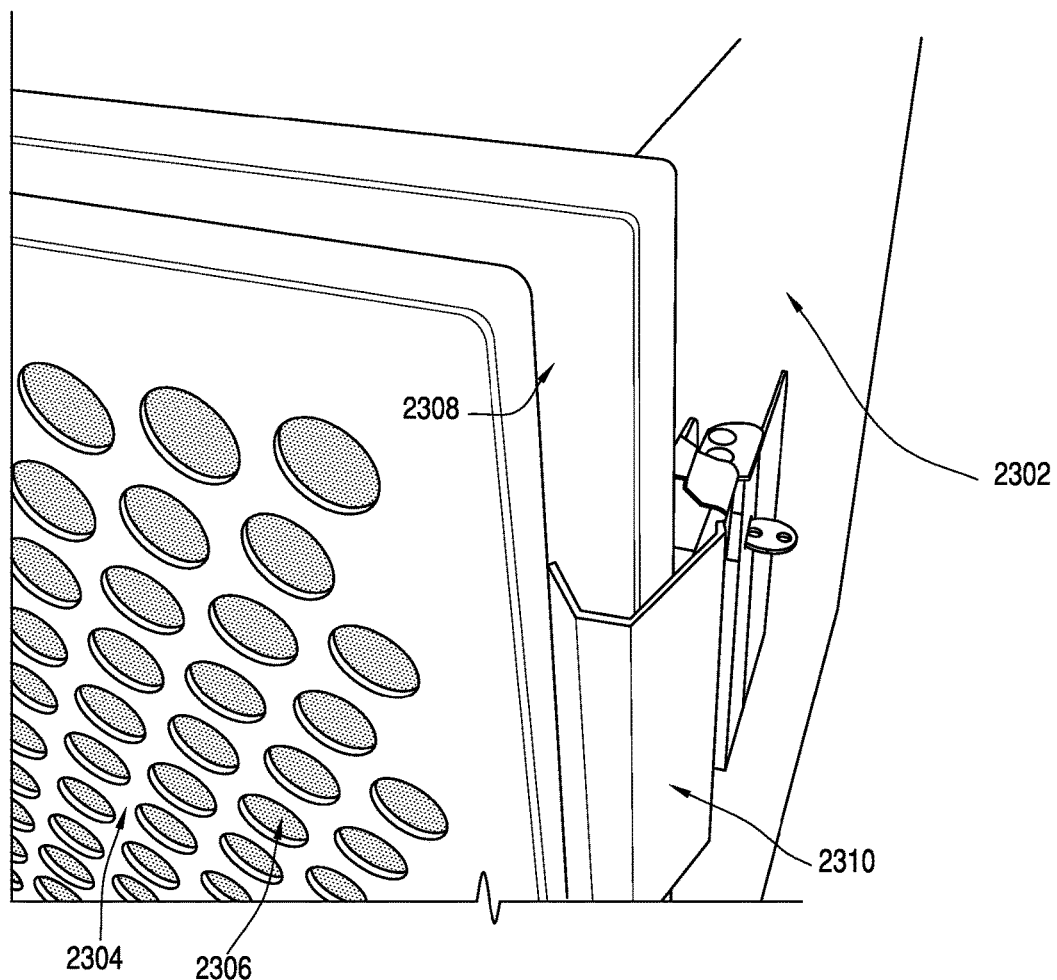
FIG. 23 is a perspective view of an exemplary sterilizing cabinet and filter door suitable for use in practicing exemplary embodiments of the present disclosure.

With reference to FIG. 23, shown is a perspective view of an exemplary sterilizing cabinet and filter door suitable for use in practicing exemplary embodiments of the present disclosure. Shown in FIG. 23 are sterilizing cabinet 2302, filter door 2304, filter cartridge 2306, clamp trough 2308, and clamp 2310. As illustrated, filter door 2304 includes clamp trough 2308 around the outer edge of filter door 2304. Exemplary embodiments of clamp trough 2308 align with the trough section of sterilizing cabinet 2302 when filter door 2304 covers the opening of sterilizing cabinet 2302. Additionally, clamp trough 2308 is sized and located such that clamp 2310 is able to latch, clamp or otherwise hook onto filter door 2304 through clamp trough 2308. Exemplary embodiments of clamp trough 2308 provides a lip or trough that substantially prevents clamp 2310 from slipping when clamp 2310 clamps onto filter door 2304.

Figure 24:
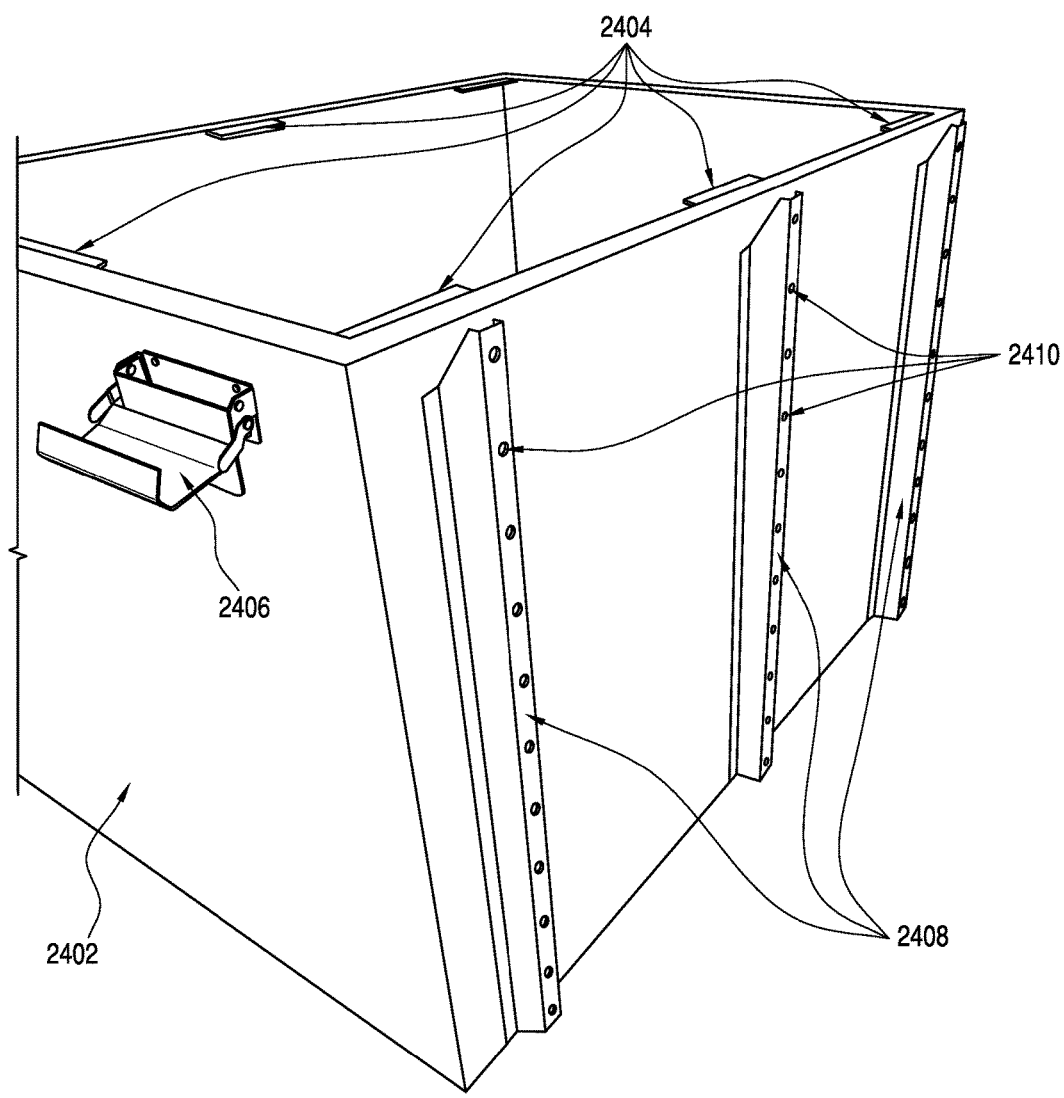
FIG. 24 is a bottom perspective view of an exemplary sterilizing cabinet suitable for use in practicing exemplary embodiments of the present disclosure.

Referring to FIG. 24, shown is a bottom perspective view of an exemplary sterilizing cabinet suitable for use in practicing exemplary embodiments of the present disclosure. Shown in FIG. 24 are sterilizing cabinet 2402, sterilizing cabinet tabs 2404, clamp 2406 and legs 2408. Exemplary embodiments of legs 2408 reside on the bottom of sterilizing cabinet 2402 and provide a stable foundation for sterilizing cabinet 2402 to rest on a surface. Exemplary embodiments of legs 2408 further include holes 2410. Holes 2410 provide a means for attaching legs 2408 and thus sterilizing cabinet 2402 to a surface. For example, sterilizing cabinet 2402 through holes 2410 on legs 2408 can be screwed, bolted, attached, or nailed onto a table, counter, or other flat surface large and structurally sturdy enough to maintain sterilizing cabinet 2402.

Figure 25:
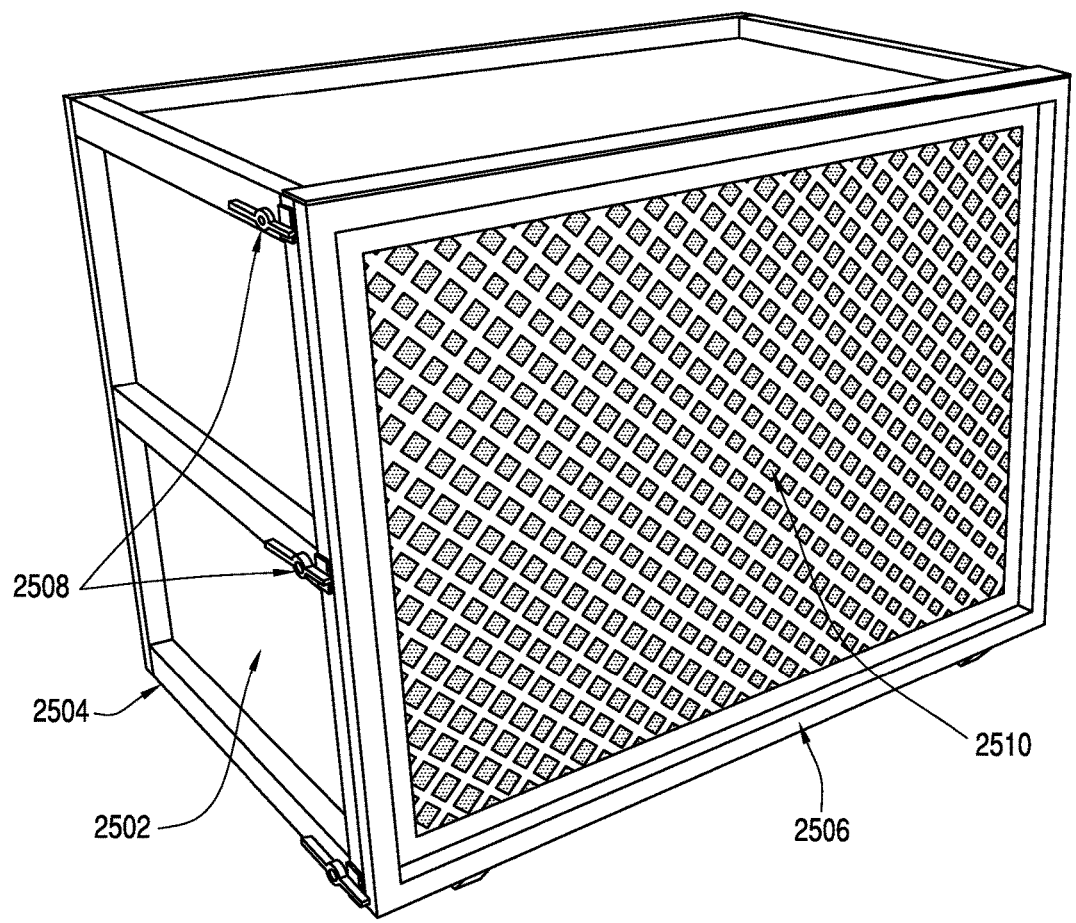
FIG. 25 is a perspective view of an alternative embodiment of a sterilizing cabinet suitable for use in practicing exemplary embodiments of this disclosure.

Referring to FIG. 25, shown is a perspective view of an alternative embodiment of a sterilizing cabinet suitable for use in practicing exemplary embodiments of this disclosure. Shown in FIG. 25 are sterilizing cabinet 2502, frame 2504, filter door 2506, latches 2508, and filter 2510. As illustrated, sterilizing cabinet 2502 is maintained within frame 2504. Frame 2504 provides a structurally reinforcing frame for sterilizing cabinet 2502. Exemplary embodiments of frame 2504 are able to securely maintain sterilizing cabinet 2502 such that all of the sides/corners of sterilizing cabinet 2502 are supported by frame 2504. Exemplary embodiments of frame 2504 are made of any type of metal, plastic, composite, or aluminum alloy. Exemplary embodiments of frame 2504 are able to repeatedly undergo sterilizing cycles (e.g., steam sterilizing cycles) and maintain its structural integrity.

Filter door 2506 attaches to frame 2504 through the use of latches 2508. However, it should be appreciated that latches 2508 can include any type of clamping, latching or clasping device known in the art that is able to releasable attach filter door 2506 to frame 2504 such that a sealed interface is created between filter door 2506 and sterilizing cabinet 2502.

Figure 26:
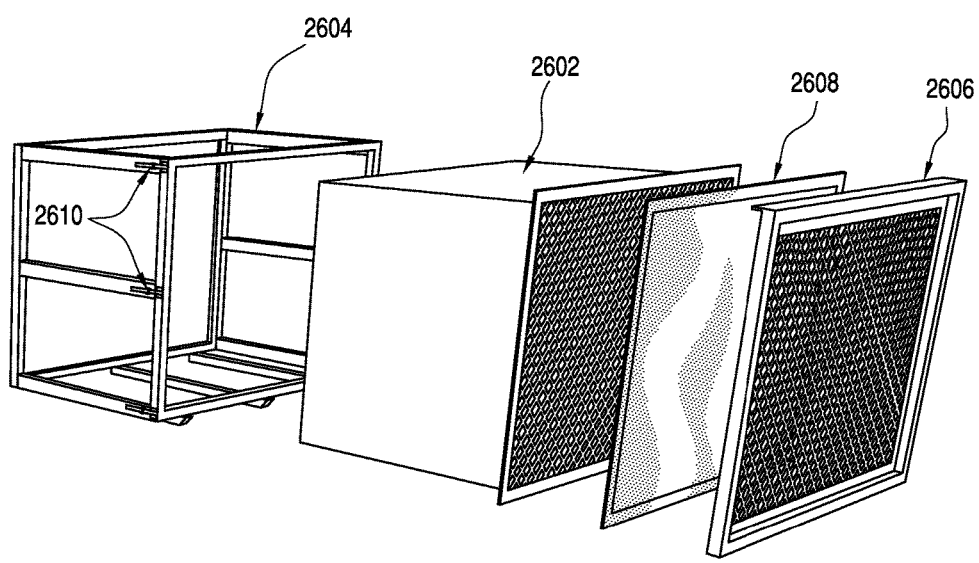
FIG. 26 is a perspective view of a separated alternative embodiment of a sterilizing cabinet suitable for use in practicing exemplary embodiments of this disclosure.

Referring to FIG. 26, shown is a perspective view of a separated alternative embodiment of a sterilizing cabinet suitable for use in practicing exemplary embodiments of this disclosure. Shown in FIG. 26 are sterilizing cabinet 2602, frame 2604, filter door 2606, filter cartridge 2608, and latches 2610. In some embodiments, as shown in FIG. 26, sterilizing cabinet 2602 can be removed from frame 2604 when filter door 2606 is released from removable frame 2604 by latches 2610. In other exemplary embodiments, frame 2604 is not removable from sterilizing cabinet 2602, but is fixedly attached to sterilizing cabinet 2602. Filter door 2606 as depicted includes a fenestrated grid throughout its center. However, exemplary embodiments of filter door 2606 include any type of arrangement of holes, gaps, or grids such that sterilizing steam is free to pass through the center portion of filter door 2606.

During a sterilizing cycle filter cartridge 2608 is maintained between filter door 2606 and sterilizing cabinet 2602. As previously stated above, filter cartridge 2608 is placed between filter door 2606 and sterilizing cabinet 2602 creating a sealed interface around its edges such that sterilizing steam is not able to pass between the sealed interface, but can only pass through the center of filter cartridge 2608.

Figure 27:
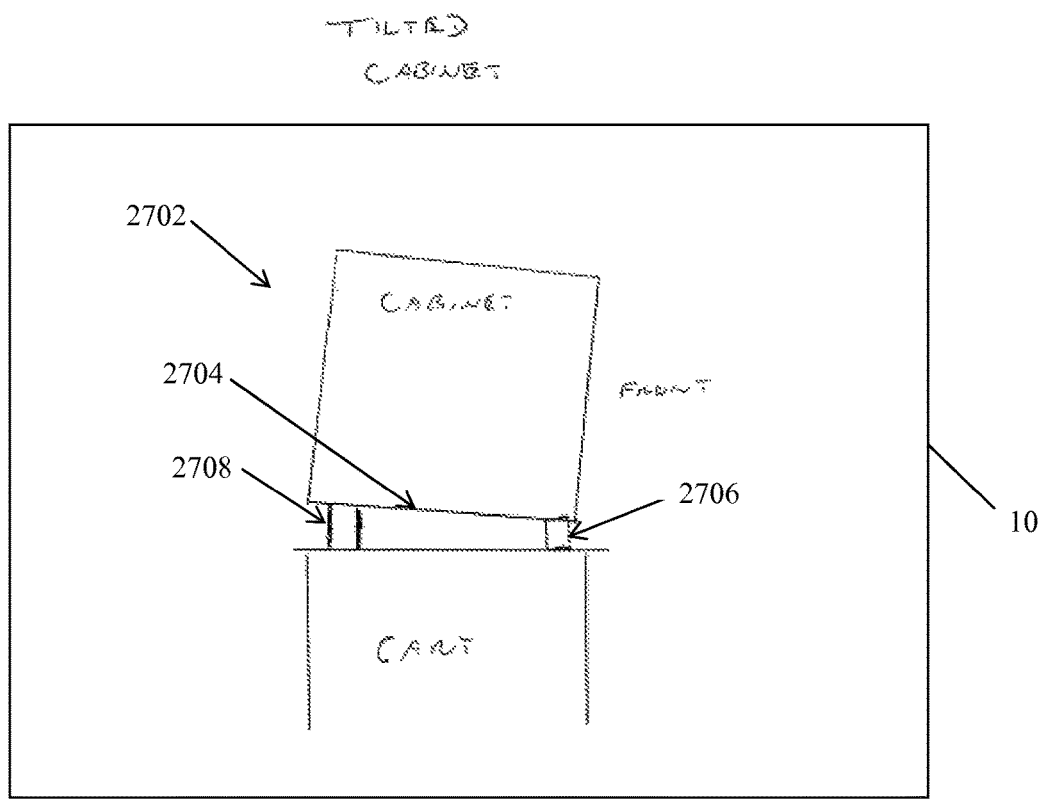
FIG. 27 is a side view of an embodiment of a sterilizing cabinet suitable for use in practicing exemplary embodiments of this disclosure.

Referring to FIG. 27, illustrated is a side view of an embodiment of a sterilizing cabinet in an autoclave 10. Shown in FIG. 27 is a sterilizing cabinet 2702 with bottom 2704, front legs 2706, and back legs 2708. Front legs 2706 and back legs 2708 as shown in FIG. 27 are pegs or stands fixedly attached to bottom 2704 of sterilizing cabinet 2702, which provide support for sterilizing cabinet 2702 when placed on a substantially planar surface. As shown in FIG. 27, there are two front legs 2706 and two back legs 2708. However, it should be appreciated that exemplary embodiments of front legs 2706 and back legs 2708 can include one or more than one leg or support provided that front legs 2706 are shorter than back legs 2708 which in turn tilts or angles bottom 2704 toward the front of sterilizing cabinet 2702. In other words, front legs 2706 and back legs 2708 include any arrangement resulting in bottom 2704 not being a level surface but tilted, inclined, towards a vent port of sterilizing cabinet 2702. Preferably, the bottom 2704 is sufficiently inclined to induce a flow of condensate to and through the vent port.

In another exemplary embodiment, sterilizing cabinet 2702 includes a single front leg 2706 that spans or substantially spans the front width of sterilizing cabinet 2702, and a single back leg 2708 that spans or substantially spans the back width of sterilizing cabinet 2702. In yet another embodiment, sterilizing cabinet 2702 includes two front legs 2706 located in opposite front corners of bottom 2704 of sterilizing cabinet 2702, and a single back leg 2708 located in the middle or substantially the middle of the back of bottom 2704 of sterilizing cabinet 2702.

In a further exemplary embodiment, front legs 2706 and back legs 2708 are adjustable such that their length or height can be manually changed. It is contemplated that sterilizing cabinet 2702 can include actuators, such as servos, pistons, or lifts that can be remotely engaged to tilt the bottom 2704 to selectively induce flow along the bottom to the vent port.

Exemplary embodiments of bottom 2704 provide a flat surface that when tilted, towards the front of sterilizing cabinet 2702 which contains a vent port and a filter, allows a liquid, such as condensate to flow along bottom 2704 to and through the filter and out of sterilizing cabinet 2702. In practice, when sterilizing cabinet 2702 undergoes a sterilization cycle, sterilizing cabinet 2702 is placed in an autoclave or other known sterilizing device. The autoclave is then shut and sterilizing steam passes through a filter or filters overlaying a front vent port to the interior of sterilizing cabinet 2702 at which point the sterilizing steam comes into contact with any items or materials within the interior of sterilizing cabinet 2702. This process can produce a substantial amount of condensate within the interior of sterilizing cabinet 2702, which can collect on the bottom 2704 of sterilizing cabinet 2702. For example, approximately 12 ounces of condensate may be produced for every 15 pounds of load maintained within sterilizing cabinet 2702 during a sterilization cycle of the autoclave. Exemplary embodiments of bottom 2704 provide a surface that allows the condensate to flow or move freely towards a filter on sterilizing cabinet 2702, such as the front of the cabinet, so that the condensate can exit the interior of sterilizing cabinet 2702. Exemplary embodiments of the sterilizing cabinet 2702 further provide for at least a substantial portion, and in select configurations all of the condensate within sterilizing cabinet 2702 to have exited sterilizing cabinet 2702 prior to the opening of the autoclave 10 or other sterilizing device. In yet another exemplary embodiment, sterilizing cabinet 2702 contains an industry acceptable amount of condensate following a sterilizing cycle, when the autoclave is opened.

Exemplary embodiments of bottom 2704 also include surfaces that are not substantially flat, but have channels, features or minor curves that move or allow to move condensate or accumulated condensate to a vent port of sterilizing cabinet 2702 through a filter or to another predetermined outlet or filtered drain that exits the interior of sterilizing cabinet 2702.

Figure 28:
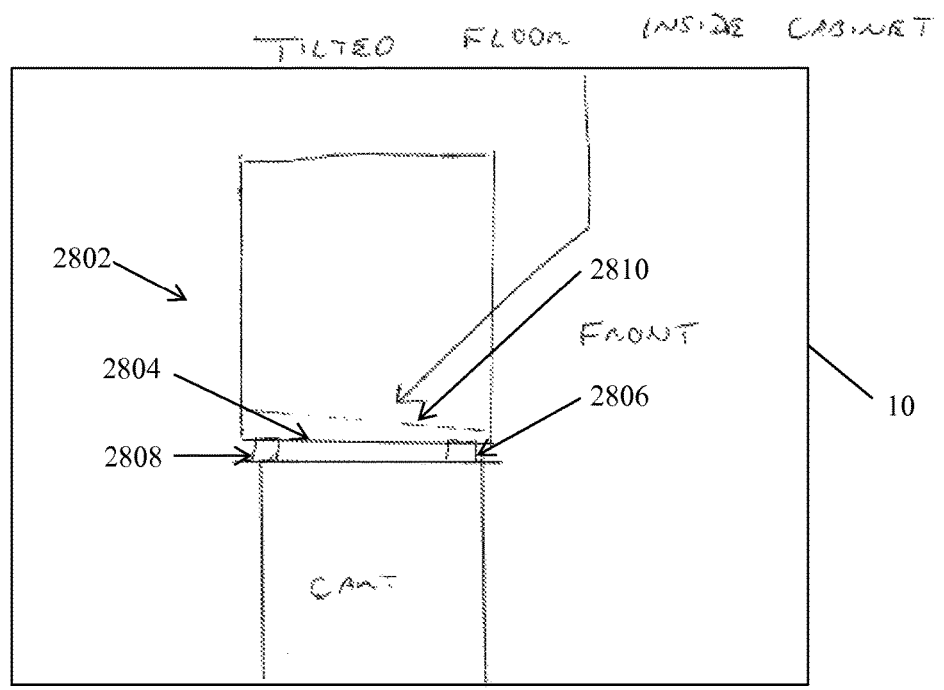
FIG. 28 is another embodiment of a sterilizing cabinet suitable for use in practicing exemplary embodiments of this disclosure.

Shown in FIG. 28 is sterilizing cabinet 2802, bottom 2804, front legs 2806, back legs 2808, and raised floor 2810 within the autoclave 10. In this embodiment, front legs 2806 and back legs 2808 are the same length or height such that bottom 2804 as well as sterilizing cabinet 2802 is level when placed on a level planar surface. Raised floor 2810 as depicted is located above bottom 2804 in the interior of sterilizing cabinet 2802.

Raised floor 2810 in one embodiment is substantially planar. Exemplary embodiments of raised floor 2810 provide a surface that allows or moves a flow of condensate toward a vent port located on the front of sterilizing cabinet 2802 and through the filter overlying the vent port. In another exemplary embodiment, raised floor 2810 is a surface that is not substantially planar, but is curved or has minor curves, or flow channels that moves or allows to move a flow of condensate or accumulated condensate to a vent port of sterilizing cabinet 2802 or to another predetermined outlet or filtered drain that exits the interior of sterilizing cabinet 2802.

Figure 29:
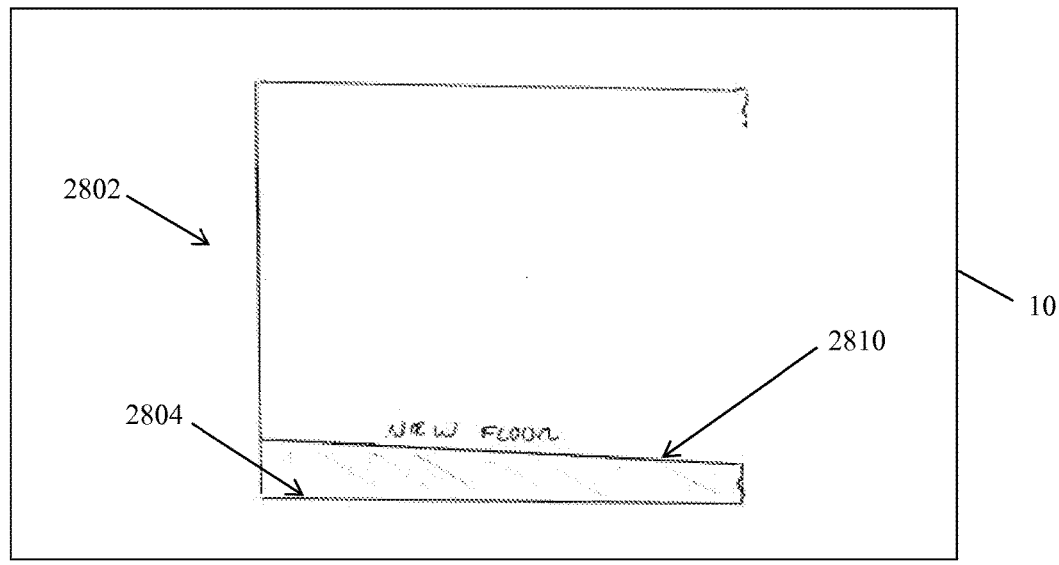
FIG. 29 is an internal view of an exemplary sterilizing cabinet suitable for use in practicing exemplary embodiments of this disclosure.

Shown in FIG. 29 is the interior of sterilizing cabinet 2802 with bottom 2804, and raised floor 2810 within the autoclave 10. As is shown, raised floor 2810 is above bottom 2804 and is angled relative to bottom 2804 such that a flow of condensate is directed toward the vent port of sterilizing cabinet 2802. It should be appreciated that exemplary embodiments of raised floor 2810 can include both substantially planar and curved or featured (with channels) embodiments that direct condensate toward a vent port on sterilizing cabinet 2802, or toward another outlet that allows condensate to drain or exit the interior of sterilizing cabinet 2802.

Figure 30:
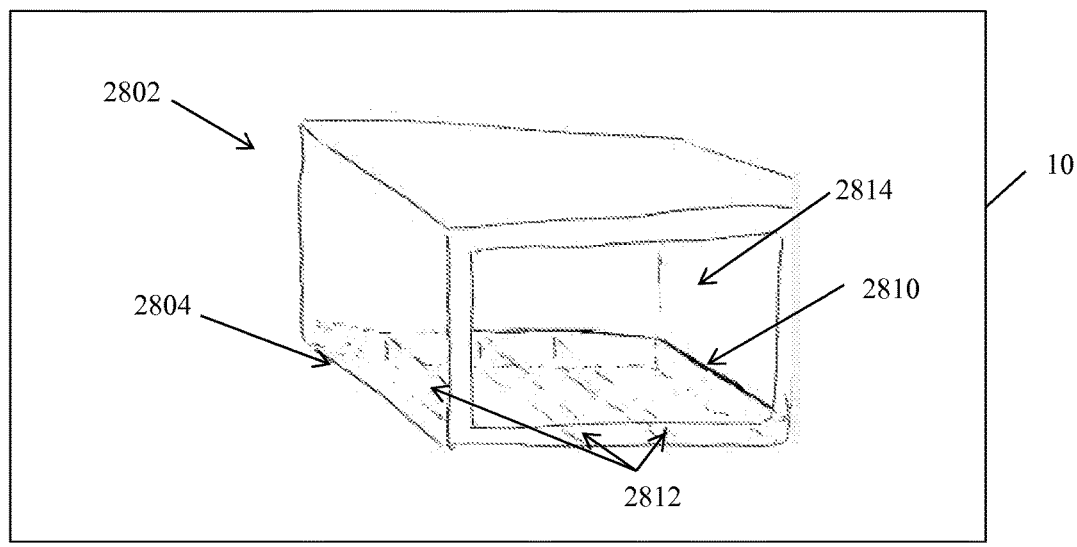
FIG. 30 is a front perspective view of an exemplary sterilizing cabinet suitable for use in practicing exemplary embodiments of this disclosure.

Shown in FIG. 30 is sterilizing cabinet 2802, bottom 2804, raised floor 2810, raised floor supports 2812, and vent port 2814 within the autoclave 10. Raised floor supports 2812 provide support for the position of raised floor 2810 with sterilizing cabinet 2802. As shown in FIG. 30, raised floor supports 2812 are beams located under raised floor 2810 that are connected to raised floor 2810 and bottom 2804 to maintain the position of raised floor 2810. It should be appreciated that raised floor supports 2812 can include any known beam or support that is able to maintain the position of raised floor 2810 with the weight of the anticipated loaded sterilizing cabinet 2802, which can be up to a 250 pound load or more.

As illustrated in FIG. 30, raised floor 2810 is flush with the bottom of vent port 2814. Exemplary embodiments of raised floor 2810 include instances wherein raised floor 2810 is flush or nearly flush with the bottom of vent port 2814. Exemplary embodiment of raised floor 2810 are positioned relative to the bottom of vent port 2814 such that a flow of condensate along raised bottom 2810 can move and progress through vent port 2814. Raised floor 2810 in the embodiment shown, is tilted or angled relative to bottom 2804 toward vent port 2814 such that any fluid or condensate on raised floor 2810 is moved towards vent port 2814.

In operation, the autoclave receives the sterilizing cabinet and subjects the sterilizing cabinet to a sterilization cycle. As set forth above, the sterilization can include, but is not limited to heat, steam, pressure, gas, plasma, irradiation, chemical components, chemical vapor or combinations thereof.

Thus, the sterilizing cabinet is retained within the autoclave, and the interior environment of the autoclave is controlled to provide a sterilization cycle. The autoclave typically creates a sealed environment which is thus applied to the retained sterilizing cabinet. The autoclave thus subjects the sterilizing cabinet and the interior of the sterilizing cabinet to the sterilization cycle.

The interface between the filters and the sterilizing cabinet is effectively sealed either prior to or during or at the completion of the sterilization cycle. That is, at least before the autoclave is opened, a sealed interface is formed between the seals and the sterilizing cabinet. It is understood the seal between the filter and the sterilizing cabinet may go through a transformation during the sterilization cycle. When the filter is initially operably located relative to the sterilizing cabinet, a seal can be formed. However, it is contemplated that the initial operable location of the seal relative to the sterilizing cabinet may not form a seal, wherein the sealed interface is formed during the sterilization cycle or at the completion of the sterilization cycle.

The seal, when exposed to the sterilization cycle, (in select cases, heat in the form of steam, and pressure) may under goes slight transformation of the seal configuration, and either becomes more form fitting to the sealing surface area or even results in seal formation. This change in the seal during the sterilization cycle may create a more robust seal than when it was originally placed. It is contemplated a variety of materials can be used to enhance or form a seal between the filter (or the cartridge) and the sterilizing cabinet, such as but not limited to card stocks, thermoplastics, thermoplastic elastomers, polymers and waxes.

Thus, the interface between the filters and the sterilizing cabinet can be dynamic, forming a seal during the sterilization cycle, or static, entering the sterilization cycle with the sealed interface and maintaining the sealed interface throughout the sterilization cycle.

Before the autoclave is opened, that is before the sterilized environment of the autoclave is exposed to ambient environment, the interior of the sterilizing cabinet should have no more than a certain amount of moisture and a seal exist between any filter, or cartridge and the sterilizing cabinet. Thus, it is advantageous for a sterilizing cabinet to have only an amount of condensate that can be driven off or evaporated by the autoclave during a normal, or given or predetermined sterilizing cycle of the autoclave or during the post-sterilization cool down period.

In conjunction with any cycle time for removing condensate, the inclined surface in the sterilizing cabinet induces a flow of the condensate to and through a port, such as a filter. The cycle time can be decreased by facilitating the removal of condensate from the sterilizing cabinet during the sterilization cycle. That is, by draining condensate from the sterilizing cabinet during the sterilization cycle, the amount of condensate to be evaporated from within the sterilizing cabinet during the sterilization cycle, or during the post-sterilization cool down period, is decreased, thereby increasing efficiency of the process.

Further exemplary embodiments according to this disclosure include the following embodiments below.

Embodiment 1

A sterilizing assembly, comprising: (a) a sterilizing cabinet; (b) a first tray and a second tray sized to be retained within the cabinet; and (c) at least one removable spacer intermediate the first tray and the second tray, the spacer being sterilizable and vertically separating the first tray and the second tray by a given height, the spacer inhibiting lateral displacement of the first tray relative to the second tray, wherein the given height is sufficient to permit a passage of a sufficient quantity of a sterilizing agent between the first tray and the second tray for a predetermined time.

Embodiment 2

The sterilizing assembly according to embodiment 1, wherein the at least one removable spacer is fenestrated.

Embodiment 3

The sterilizing assembly according to embodiment 1, further comprising a second removable spacer, the second removable spacer being sterilizable and located intermediate to one of the first tray and the second tray and the sterilizing cabinet.

Embodiment 4

The sterilizing assembly according to embodiment 1, wherein the given height is at least 0.1 inches.

Embodiment 5

The sterilizing assembly according to embodiment 1, wherein the given height is sufficient to permit passage of a sterilizing agent.

Embodiment 6

The sterilizing assembly according to embodiment 1, wherein the at least one removable spacer includes a shaped wire.

Embodiment 7

The sterilizing assembly according to embodiment 1, wherein the first tray defines an open top and the at least one removable spacer is sized to span the open top.

Embodiment 8

The sterilizing assembly according to embodiment 1, wherein the first tray is free of a lid.

Embodiment 9

The sterilizing assembly according to embodiment 1, wherein the at least one removable spacer and the second removable spacer are sterilizable only once.

Embodiment 10

A method of loading a sterilizing cabinet, the method comprising: (a) loading a sterilizable first pan and a sterilizable second pan within the sterilizing cabinet; and (b) placing a removable and sterilizable spacer between the first pan and the second pan, the spacer (i) providing at least one of a predetermined vertical spacing between the first pan and the second pan and (ii) inhibiting horizontal displacement of the first pan relative to the second pan.

Embodiment 11

The method according to embodiment 10, wherein at least one of the first pan and the second pan is lid free.

Embodiment 12

The method according to embodiment 10, wherein the vertical spacing is sufficient to permit passage of a sterilizing agent.

Embodiment 13

The method according to embodiment 10, wherein the predetermined vertical spacing is at least 0.1 inches.

Embodiment 14

The method according to embodiment 10, further comprising loading a sterilizable third pan and a sterilizable fourth pan within the sterilizing cabinet and placing a second sterilizable spacer to individually vertically space the sterilizable second pan relative to the sterilizable third pan and placing a third sterilizable spacer to individually vertically space the sterilizable third pan relative to the fourth pan independent of the first pan and the second pan.

Embodiment 15

The method according to embodiment 10, wherein the sterilizable spacer between the first pan and the second pan provides a predetermined vertical spacing between the first pan and the second pan.

Embodiment 16

A method of sterilizing, the method comprising: (a) loading a tray retaining a surgical instrument in a sterilization cabinet; (b) sealing a primary filter relative to a vent port in the sterilization cabinet; (c) sealing a secondary filter relative to the vent port and independent of the primary filter; and (d) passing a sterilizing agent through the secondary filter and the primary filter. For the purposes of this disclosure surgical instruments includes implantable materials or devices as well as instruments used for conducting surgeries and medical procedures.

Embodiment 17

The method according to embodiment 16, further comprising removing the secondary filter to retain the sealed primary filter and sterilization cabinet.

Embodiment 18

A sterilizable pan assembly, comprising: (a) a first sterilizable pan having an open top, a closed bottom and a pair of projecting spacer legs; and (b) a second sterilizable pan having an open top and a closed bottom, (c) the spacer legs configured to releasably engage a portion of the second pan and maintain a predetermined vertical spacing between the bottom of the first pan and the top of the second pan.

Embodiment 19

The sterilizable pan assembly according to embodiment 18, wherein the predetermined vertical spacing between the bottom of the first pan and the top of the second pan is at least 0.1 inches.

Embodiment 20

The sterilizable pan assembly according to embodiment 18, wherein the predetermined vertical spacing between the bottom of the first pan and the top of the second pan is sufficient to permit passage of a sterilizing agent.

Embodiment 21

A filtering assembly, comprising: (a) a primary filter holding portion for holding a primary filter for overlying a vent port and forming a sealed interface with a sterilizing cabinet; and (b) a secondary filter holding portion for holding a secondary filter, moveably attached to the primary filter holding portion for overlying the primary filter holding portion and forming a sealed interface with the primary filter holding portion.

Embodiment 22

The filtering assembly according to embodiment 21, wherein the primary filter and the secondary filter are different colors.

Embodiment 23

The filtering assembly according to embodiment 21, wherein the primary filter holding portion and the secondary filter holder portion are hingedly attached.

Embodiment 24

The filtering assembly according to embodiment 21, wherein the secondary filter and the primary filter are coextensive.

Embodiment 25

The filtering assembly according to embodiment 21, wherein the secondary filter and the primary filter have different filter properties.

Embodiment 26

The filtering assembly according to embodiment 21, wherein the secondary filter and the primary filter have similar filter properties.

Embodiment 27

A filter comprising: (a) a center portion of porous material with a predetermined density; and (b) an edge portion of porous material.

Embodiment 28

The filter according to embodiment 27, wherein the edge portion further comprises raised silicone beads.

Embodiment 29

The filter according to embodiment 27, wherein the edge portion is thicker than the center portion.

Embodiment 30

The filter according to embodiment 27, wherein the edge portion comprises at least two layers of folded material.

Embodiment 31

The filter according to embodiment 27, wherein the predetermined density of the center portion allows for passage of a sterilizing agent through the center portion and prevents passage of non-gaseous agents.

Embodiment 32

A filter cartridge, the filter cartridge comprising: (a) a frame, the frame comprising a rigid or flexible edge portion and defining a hollow center portion; and (b) a filter, the filter comprising a porous material and being affixed to the frame, the porous material being able to pass only gaseous materials through its surface, wherein the filter cartridge provides sufficient integrity to form a sealed interface with a confronting surface.

Embodiment 33

The filter cartridge according to embodiment 32, the filter cartridge further comprising a second filter, the second filter comprising a porous material and being affixed to the frame, the porous material being able to pass only gaseous materials through its surface.

Embodiment 34

The filter cartridge according to embodiment 32, the filter cartridge further comprising a second frame, the second frame comprising a rigid or flexible edge portion and defining a hollow center portion, the second frame being affixed to the filter.

Embodiment 35

The filter cartridge according to embodiment 34, the filter cartridge further comprising a second filter, the second filter comprising a porous material and being affixed to the second frame and the filter, the porous material being able to pass only gaseous materials through its surface.

Embodiment 36

The filter cartridge according to embodiment 32, wherein the filter is removeably affixed to the frame.

Embodiment 37

The filter cartridge according to embodiment 32, wherein the frame and filter are coextensive.

Embodiment 38

The filter cartridge according to embodiment 32, wherein the frame and the filter are integral.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:
1. A sterilizing cabinet assembly, comprising:
    (a) a cabinet having an access port and a bottom;
    (b) a door connected to the cabinet, the door moveable between an open position permitting passage through the access port to an interior of the cabinet and a closed position precluding passage through the access port;
    (c) at least one of a sidewall of the cabinet and the door having a vent port, wherein the bottom is port-free and configured to induce condensate on the bottom to flow to the vent port on the at least one of the sidewall of the cabinet and the door; and
    (d) a filter overlying the vent port and forming a sealed interface with an adjacent portion of the one of the cabinet and the door.
2. The sterilizing cabinet assembly according to claim 1, wherein the bottom is an inclined surface, the inclined surface having a high portion and a low portion, and wherein the low portion is adjacent to the vent port.
3. The sterilizing cabinet assembly according to claim 1, wherein the bottom comprises a surface and a raised inclined surface, the raised inclined surface overlying a portion of the surface and comprising a high portion and a low portion, wherein the low portion is adjacent to the vent port.
4. The sterilizing cabinet assembly according to claim 1, the sterilizing cabinet assembly further comprising at least one protruding surface configured to support the sterilizing cabinet on a substantially planar surface, the at least one protruding surface further configured to induce a flow of condensate along the bottom toward the vent port, and wherein the bottom is planar.
5. The sterilizing cabinet assembly according to claim 4, wherein the at least one protruding surface comprises at least four legs, and wherein two adjacent legs of the at least four legs have a length equal to one another, the length being shorter than a remainder of the at least four legs.
6. The sterilizing cabinet assembly according to claim 4, wherein the at least one protruding surface comprises at least four legs, and wherein three legs of the at least four legs have a length equal to one another, the length being shorter than a remainder of the at least four legs.

7. The sterilizing cabinet assembly according to claim 4, wherein the at least one protruding surface comprises at least three legs coupled to the bottom, and wherein two of the at least three legs have a length equal to one another that is shorter than a remainder of the at least three legs.

8. A method of sterilizing, the method comprising:
(a) occluding a vent port located on one of a sidewall and a door of a sterilizing cabinet with a filter, the sterilizing cabinet having an internal, port-free, inclined surface to induce a condensate flow to the vent port on one of a sidewall and a door of the sterilizing cabinet;
(b) performing a sterilization cycle on the sterilizing cabinet; and
(c) draining along the internal, port-free, inclined surface in the sterilizing cabinet at least a portion of a condensate formed in the sterilization cycle to pass from the sterilizing cabinet through the filter of the vent port located on one of a sidewall and a door.

9. The method according to claim 8, wherein the sterilization cycle comprises passing sterilizing steam through the vent port.

10. The method according to claim 8, wherein the sterilizing cabinet includes a floor and the floor comprises the inclined surface.

11. The method according to claim 8, wherein the sterilizing cabinet includes a bottom and the inclined surface is spaced from and raised above the bottom.

12. The method according to claim 8, wherein the bottom comprises at least one protruding surface configured to support the sterilizing cabinet on a substantially planar surface, the at least one protruding surface further configured to induce a flow of condensate on the bottom toward the vent port, and wherein the bottom is planar.

13. The method according to claim 12, wherein the at least one protruding surface comprises at least four legs, and wherein two adjacent legs of the at least four legs have a length equal to one another, the length being shorter than a remainder of the at least four legs.

14. The method according to claim 12, wherein the at least one protruding surface comprises at least four legs, and wherein three legs of the at least four legs have a length equal to one another, the length being shorter than a remainder of the at least four legs.

15. The method according to claim 12, wherein the at least one protruding surface comprises at least three legs coupled to the bottom, and wherein two of the at least three legs have a length equal to one another that is shorter than a remainder of the at least three legs.

16. A method for sterilizing, the method comprising:
(a) locating a sterilizing cabinet in an autoclave;
(b) applying a sterilization cycle to the sterilizing cabinet in the autoclave; and
(c) draining along an internal, port-free, inclined surface in the sterilizing cabinet at least a portion of a condensate to pass from the sterilizing cabinet through a vent port in one of a sidewall and a door of the sterilizing cabinet during the sterilization cycle.

17. The method according to claim 16, wherein draining at least a portion of a condensate includes draining the condensate through the vent port of the sterilizing cabinet prior to opening the autoclave.

18. The method according to claim 16, wherein draining at least a portion of a condensate includes passing the at least a portion through the sidewall of the sterilizing cabinet.

19. The method according to claim 16, wherein draining at least a portion of a condensate includes draining the at least a portion of the condensate through a filter.

20. The method according to claim 16, wherein draining at least a portion of a condensate includes draining the at least a portion of the condensate through a filter in the vent port.

* * * * *